(12) United States Patent
Haick et al.

(10) Patent No.: US 8,481,324 B2
(45) Date of Patent: Jul. 9, 2013

(54) APPARATUS AND METHODS FOR DIAGNOSING RENAL DISORDERS

(75) Inventors: Hossam Haick, Haifa (IL); Zaid Abassi, Haifa (IL); Farid Nakhoul, Shefaram (IL)

(73) Assignee: Technion Research and Development Foundation Ltd. (IL)

( * ) Notice: Subject to any disclaimer, the term of this patent is extended or adjusted under 35 U.S.C. 154(b) by 45 days.

(21) Appl. No.: 13/131,345

(22) PCT Filed: Dec. 2, 2009

(86) PCT No.: PCT/IL2009/001137
§ 371 (c)(1),
(2), (4) Date: May 26, 2011

(87) PCT Pub. No.: WO2010/064239
PCT Pub. Date: Jun. 10, 2010

(65) Prior Publication Data
US 2011/0244584 A1    Oct. 6, 2011

Related U.S. Application Data

(60) Provisional application No. 61/119,741, filed on Dec. 4, 2008.

(51) Int. Cl.
*G01N 33/48* (2006.01)
*G01N 27/04* (2006.01)
*G01N 27/22* (2006.01)
*G01N 1/22* (2006.01)

(52) U.S. Cl.
USPC ............ 436/63; 436/64; 436/73; 436/80; 436/84; 436/96; 436/111; 436/112; 436/128; 436/149; 436/181; 422/84; 506/7

(58) Field of Classification Search
USPC ............ 436/63, 64, 71, 73, 80, 84, 96, 106, 436/111, 112, 128, 149, 151, 181; 422/83, 422/84, 88, 90, 91, 98; 506/7
See application file for complete search history.

(56) References Cited

U.S. PATENT DOCUMENTS 6,312,390 B1    11/2001    Phillips
6,411,905 B1    6/2002    Guoliang (Continued)

FOREIGN PATENT DOCUMENTS

| WO | 2008/039165 | 4/2008 |
| WO | 2008/052104 | 5/2008 |
| WO | 2009/066293 | 5/2009 |
| WO | 2009/144725 | 12/2009 |

OTHER PUBLICATIONS

Lu et al. Journal of Electroanalytical Chemistry, vol. 593, 2006, pp. 105-110.*

(Continued)

*Primary Examiner* — Maureen Wallenhorst
(74) *Attorney, Agent, or Firm* — St. Onge Steward Johnston & Reens LLC

(57) ABSTRACT

The present invention provides a system containing an array of chemically sensitive sensors based on coated single walled carbon nanotubes, for measuring volatile organic compounds indicative of renal failure. Methods of breath analysis for diagnosing chronic, acute and end-stage renal failure are disclosed.

11 Claims, 18 Drawing Sheets

U.S. PATENT DOCUMENTS

| | | | |
|---|---|---|---|
| 6,589,748 | B2 | 7/2003 | Comper |
| 6,606,566 | B1 | 8/2003 | Sunshine |
| 6,609,068 | B2 | 8/2003 | Cranley |
| 6,620,109 | B2 | 9/2003 | Hanson, III |
| 6,767,732 | B2 | 7/2004 | Alocilja |
| 6,773,926 | B1 | 8/2004 | Freund |
| 6,820,012 | B2 | 11/2004 | Sunshine |
| 6,839,636 | B1 | 1/2005 | Sunshine |
| 6,841,391 | B2 | 1/2005 | Lewis |
| 7,052,854 | B2 | 5/2006 | Melker |
| 7,076,371 | B2 | 7/2006 | Fu |
| 7,138,229 | B2 | 11/2006 | Hu |
| 7,153,272 | B2 | 12/2006 | Talton |
| 7,547,931 | B2 | 6/2009 | Star |
| 2002/0117659 | A1 | 8/2002 | Lieber |
| 2005/0054942 | A1 | 3/2005 | Melker |
| 2007/0048180 | A1 | 3/2007 | Gabriel |
| 2007/0106168 | A1 | 5/2007 | O'Neil |
| 2008/0021339 | A1 | 1/2008 | Gabriel |
| 2010/0273665 | A1* | 10/2010 | Haick et al. .................. 506/8 |
| 2011/0098591 | A1* | 4/2011 | Haick et al. .................. 600/532 |

OTHER PUBLICATIONS

Peng et al. Nanoletters, vol. 8, No. 11, Oct. 8, 2008, pp. 3631-3635.*
Qi et al. Nanoletters, vol. 3, No. 3, Feb. 6, 2003, pp. 347-351.*
Lin et al. Sensors and Actuators B, vol. 76, 2001, pp. 177-180.*
Gelperin et al. Journal of Breath Research, vol. 2, 2008, pp. 1-6.*
Lee et al. Journal of the American Chemical Society, vol. 130, Jan. 12, 2008, pp. 1766-1773.*
Haick et al. Acsnano, vol. 3, No. 5, Apr. 27, 2009, pp. 1258-1266.*
Aspnes, D. E. and Theeten, J. B. (1980) Spectroscopic analysis of the Interface Between Si and Its Thermally Grown Oxide. J Electrochem Soc127(6):1359-1365.
Buszewski, Boguslaw et al., (2007) Human exhaled air analytics: biomarkers of diseases. Biomed Chromatogr 21(6):553-566.
Cao, Wenqing and Duan, Yixiang (2007) Current status of methods and techniques for breath analysis. Critical Reviews in Analytical Chemistry 37(1):3-13.
Chen, Xing et al., (2005) A study of an electronic nose for detection of lung cancer based on a virtual SAW gas sensors array and imaging recognition method. Measurement Science and Technology 16(8):1535-1546.
Coelho, Leiliane et al., (2007) Breath air analysis and its use as a biomarker in biological monitoring of occupational and environmental exposure to chemical agents. J Chromatography B 853(1-2):1-9.
Di Natale, Corrado et al., (1999) Electronic nose analysis of urine samples containing blood. Physiol Meas 20(4):377-384.
Dovgolevsky, Ekaterina and Haick, Hossam (2008) Direct observation of the transition point between quasi-spherical and cubic nanoparticles in a two-step seed-mediated growth method. Small 4(11):2059-2066.
Fend, Reinhard et al., (2004) Monitoring haemodialysis using electronic nose and chemometrics. Biosensors and Bioelectronics 19(12):1581-1590.
Gelperin, A. and Johnson, A. T. C. (2008) Nanotube-based sensor arrays for clinical breath analysis. J Breath Res 2(3):037015 (6 pages).
Gordon, Sydney M. et al., (2002) Volatile organic compounds as breath biomarkers for active and passive smoking. Environ Health Perspect 110(7):689-698.
Groves, William A. et al., (1998) Analyzing organic vapors in exhaled breath using a surface acoustic wave sensor array with preconcentration: selection and characterization of the preconcentrator adsorbent. Analytica Chimica Acta 371(2-3):131-143.
Kastler, Marcel et al., (2005) Influence of Alkyl Substituents on the Solution- and Surface-Organization of Hexa-perihexabenzocoronenes. J Am Chem Soc 127(12):4286-4296.
Kuzmych, Oleksandr et al., (2007) Carbon nanotube sensors for exhaled breath components. Nanotechnology 18 (37):375502 (7 pages).
Lee, Youngmi and Kim, Jiyeon (2007) Simultaneous Electrochemical Detection of Nitric Oxide and Carbon Monoxide Generated from Mouse Kidney Organ Tissues. Anal Chem 79(20):7669-7675.
Lin, Yu-Jiuan et al., (2001) Application of the electronic nose for uremia diagnosis. Sensors and Actuators B 76 (1-3):177-180.
Lu, Yijiang et al., (2006) A carbon nanotube sensor array for sensitive gas discrimination using principal component analysis. Journal of Electroanalytical Chemistry 593(1-2):105-110.
Mashiach, Elisheva et al., (1998) Renal ischemia-reperfusion injury: contribution of nitric oxide and renal blood flow. Nephron 80(4):458-467.
Mazzone, Peter J. et al., (2007) Diagnosis of lung cancer by the analysis of exhaled breath with a colorimetric sensor array. Thorax 62(7):565-568.
Mazzone, P. (2008) Progress in the development of a diagnostic test for lung cancer through the analysis of breath volatiles. J Breath Res 2(3):037014.
Meyer, Timothy W. and Hostetler, Thomas H. (2007) Uremia. N Engl J Med 357(13):1316-1325.
O'Sullivan, C. K. & Guilbault, G. G. (1999) Commercial quartz crystal microbalances—theory and applications. Biosensors & Bioelectronics 14(8-9):663-670.
Ouyang, Gangfeng and Pawliszyn, Janusz (2006) SPME in environmental analysis. Anal Bioanal Chem 386 (4):1059-1073.
Parikh, Kunjal et al., (2006) Flexible vapour sensors using single walled carbon nanotubes. Sensors and Actuators B: Chemical 113(1):55-63.
Paska, Yair et al., (2011) Enhanced Sensing of Nonpolar VolatileOrganic Compounds by SiliconNanowire Field Effect Transistors. ACS Nano 5(7):5620-5626.
Peng, Gang et al., (2008) Detecting simulated patterns of lung cancer biomarkers by random network of single-walled carbon nanotubes coated with nonpolymeric organic materials. Nano Lett 8(11):3631-3635.
Peng, Gang et al., (2009) Detection of Nonpolar Molecules by Means of Carrier Scattering in Random Networks of Carbon Nanotubes: Toward Diagnosis of Diseases via Breath Samples. Nano Lett 9(4):1362-1368.
Simenhoff, Michael L. et al., (1977) Biochemical profile or uremic breath. N Eng J Med 297(3):132-135.
Toda, Kei et al., (2006) Measurement of ammonia in human breath with a liquid-film conductivity sensor. Anal Chem 78(20):7284-7291.
Voss, Andreas et al., (2005) Smelling renal dysfunction via electronic nose. Ann Biomed Eng 33(5):656-660.
Wang, H. T. et al., (2007) Electrical detection of kidney injury molecule-1 with AlGaN/GaN high electron mobility transistors. Applied Physics Letters 91:222101-222103.
Yu, Hao et al., (2003) Detection volatile organic compounds in breath as markers of lung cancer using a novel electronic nose. Sensors, Proceedings of IEEE 2:1333-1337.
Zhao, Xiao-Mei et al., (1997) Soft lithographic methods for nanofabrication. J Mater.Chem 7:1069-1074.
Zilberman, Yael et al., (2009) Sponge-like Structures of Hexa-perihexabenzocoronenes Derivatives Enhances the Sensitivity of Chemiresistive Carbon Nanotubes to Nonpolar Volatile Organic Compounds. Langmuir 25(9):5411-541.
American Thoracic Society (ATS) and the European Respiratory Society (ERS)., ATS/ERS recommendations for standardized procedures for the online and offline measurement of exhaled lower respiratory nitric oxide and nasal nitric oxide, 2005. Am J Respir Crit Care Med 171(8):912-930.
ISR of PCT/IL09/01137 mailed May 12, 2010.

* cited by examiner

APPARATUS AND METHODS FOR DIAGNOSING RENAL DISORDERS

REFERENCE TO CO-PENDING APPLICATIONS

Priority is claimed as a U.S. national entry under 35 U.S.C. 371 of PCT/IL2009/001137, filed on Dec. 2, 2009; which claims priority to US provisional patent application Ser. No. 61/119,741, filed on Dec. 4, 2008.

FIELD OF THE INVENTION

The present invention relates to apparatus and methods for diagnosing renal failure and in particular acute renal failure and chronic renal failure through the detection of breath biomarkers.

BACKGROUND OF THE INVENTION

Renal failure is a condition that affects millions of people worldwide. It is characterized by shrinkage of the kidneys and progressive scarring within the kidneys, accompanied by excessive straining of the blood (hyperfiltration) by the remaining functional nephrons. The process of hyperfiltration often causes further reduction in kidney function that leads to a decrease in the ability of the kidneys to excrete wastes, concentrate urine, conserve electrolytes and maintain fluid balance. Yet, it is not until over 70% of the combined function of both kidneys is lost that most patients begin to experience symptoms of renal failure.

Renal failure can be divided into two main categories, namely, acute renal failure and chronic renal failure. Acute renal failure is characterized by a sudden decrease in kidney function which may occur following exposure to various therapeutic agents, radiotherapy or exposure to heavy metals and organic solvents. Chronic renal failure is more prevalent in elderly population and is often secondary to hypertension, diabetes, hyperlipidemia, and cardiovascular diseases. Renal failure can also result from cancer.

Untreated acute and chronic renal failure may progress into end stage renal disease wherein endogenous kidney function is irreversibly lost, a condition which renders the patient dependent upon dialysis or kidney transplantation. Approximately 90% of end stage renal disease is attributed to untreated chronic renal failure, whereas only 10% is attributed to acute renal failure.

The diagnosis of renal failure is usually performed by measuring the glomerular filtration rate (GFR) which provides an assessment of the filtering performance of the kidney nephrons. The two major markers used for determining GRF are urea and creatinine. In kidney failure, these markers which are normally excreted by the kidneys into the urine, are retained in the blood (reviewed by Carlson & Harrington in *Diseases of The Kidney*, 5<sup>th</sup> Ed., (Schrier & Gottschalk Eds.), Boston, Little Brown, 1993, p. 361; and Silkensen & Kasiske in *The Kidney*, 7<sup>th</sup> Ed., (Brenner Ed.), Philadelphia, 2003, p. 1107).

Although urea has been used as one of the first indicators for measuring GFR, recent studies have shown that urea is in effect a poor marker for determining GFR values. This is attributed to the many factors which influence plasma urea concentrations including, a dietary regimen with elevated protein intake, alcohol abuse and chronic liver disease. Other factors which influence urea levels in the blood are the state of hydration and tubular urea re-absorption. Additionally, some substances interfere with the accurate determination of plasma urea concentrations, including acetohexamide, allantoin, aminosalicylic acid, bilirubin, chloral hydrate, dextran, free hemoglobin, hydantoin derivatives, lipids (hyperlipidemia), sulfonamides, thiourea, and uric acid.

Creatinine is a metabolic product of creatine and phosphocreatine, which are both found almost exclusively in the muscle. Creatinine production is thus proportional to muscle mass and has little daily variability. Creatinine waste is transported through the bloodstream to the kidneys which filter out most of the creatinine. The level of creatinine in the urine and in the blood is thus indicative of kidney function. There are, however, several substances which affect the levels of creatinine including some commonly used medications (e.g. cimetidine, trimethoprim, pyrimethamine, and dapsone).

The hitherto known methods for diagnosing renal failure include physical examination wherein symptoms such as oral ulcers and pallor may indicate kidney disorder among other diseases and disorders. Blood tests and urinalysis are commonly used, wherein high levels of creatinine and blood urea nitrogen (BUN) are usually attributed to a decline in kidney filtration. As indicated previously, these tests tend to be highly inaccurate and may remain within the normal range even while 65%-75% of kidney fiinction is lost. Imaging techniques are also applied to detect changes in size, texture and position of the kidneys. These measurements are performed using ultrasound and are suitable for patients suffering from progressive renal failure.

Presently, renal biopsy remains the most definitive test to specifically diagnose chronic and acute renal failure. This method is invasive and thus includes the risk of bleeding among other possible complications. Furthermore, accurate interpretation of renal biopsy requires the expertise of a pathologist with extensive experience in analyzing biopsies.

Several markers have been re cently identified as being indicative of various kidney disorders, among which are $\beta_2$-microglobulin, N-Acetyl-Glucosaminidase (NAG), Immunoglobulin G (IgG), transferrin, and interleukin-6. Particularly important biomarkers are secondary and tertiary amines, including dimethylamine and trimethylamine which were shown to be elevated in exhaled breath of end-stage renal disease patients (Simenhoffet et al., *N. Eng. J. Med.*, 297, 132, 1977). U.S. Pat. No. 6,589,748 discloses a method of diagnosing early stages of renal diseases comprising separating all proteins in a urine sample and detecting a modified form of a protein in the sample indicative of an early stage of the renal disease. Proteins which can be used for this method are preferably albumin, globulin, euglobulin and pseudoglobulin. U.S. Pat. No. 7,138,229 provides a method for detecting kidney disease markers from a urine sample using reagents for the detection of a CXCR3 ligand or CCR-5 receptor ligand. Wang et al. (*Appl. Phys. Lett.*, 91, 222101, 2007) teaches the use of AlGaN/GaN high electron mobility transistors functionalized with specific antibodies for the detection of a kidney injury disease biomarker (KIM-1) in the blood.

Electronic nose devices were shown to be applicable for the detection of renal dysfunction. Natale et al. (*Physiol. Meas.*, 20, 377, 1999) discloses the use of quartz microbalance (QMB) sensors coated with different metallo-porphyrins for detecting traces of blood and quantitatively evaluating the pH and the specific weight of urine samples. Fend et al. (*Biosens. & Bioelectro.*, 19, 1581, 2004) discloses the use of sensors of conducting polymers based on polyaniline for monitoring haemodialysis. The results were compared to traditional biochemistry analysis of urea, creatinine, carbon dioxide, phosphate and calcium phosphate products in the blood. The conducting polymer sensors along with principle component analysis and hierarchical cluster analysis provided discrimination of pre-dialysis blood from post-dialysis blood.

Breath analysis for the diagnosis of uremia using an electronic nose device was demonstrated by Lin et al. (*Sens. & Actuat. B*, 76, 177, 2001). A sensor module composed of six 12 MHz AT-cut quartz crystals array coated with probe peptides designed by simulating the olfactory receptor protein docking with target gas molecules in combination with discriminating analysis, were used. Breath analysis of normal subjects, patients with uremia, patients with chronic renal insufficiency (CRI) and patients with chronic renal failure (CRF) provided discrimination with a correct classification of 86.78%.

Voss et al. (*Ann. Biomed. Engin.*, 33(5), 656, 2005) disclosed the application of an electronic nose system based on doped semiconductor metal oxide gas sensors for studying human body odor in patients with different stages of renal insufficiency. Principle component analysis (PCA) followed by quadratic discriminant analysis produced discrimination of all healthy subjects from renal patients and further discrimination of dialysis patients from patients with chronic renal failure with a correct classification of 95.2% for two principle odor components and 98.4% for three principle odor components.

There is an unmet need for diagnosing renal insufficiencies with adequate sensitivity and specificity in order to provide a large-scale screening technique for subjects at increased risk of developing renal dysfunction, feasible for clinical practice. Furthermore, there remains a challenge for the early detection of acute and chronic renal failure of various etiologies.

SUMMARY OF THE INVENTION

The present invention provides a system comprising an array of sensors for measuring volatile organic compounds as biomarkers for diagnosis, prognosis and monitoring of renal insufficiencies. In particular, the system of the present invention comprises an array of sensors comprising a (semi-) conductive random network of single-walled carbon nanotubes (SWCNTs) coated with an organic coating which comprises oligomers or polymers modified with at least one polar functional group, in conjunction with learning and pattern recognition algorithms. In particular embodiments, the sensor array further comprises metal nanoparticles capped with an organic coating. The present invention further provides methods of using a system comprising an array of sensors comprising SWCNTs coated with an organic coating, wherein the organic coating comprises non-polar organic molecules or organic molecules that are modified with at least one polar functional group, in conjunction with learning and pattern recognition algorithms for measuring breath analytes indicative of acute renal failure and chronic renal failure.

The present invention is based in part on the unexpected finding that diagnosis of breath samples obtained from rat models of acute, chronic and/or end-stage renal failure can be performed using sensors of SWCNTs coated with polar or non-polar, monomeric, oligomeric or polymeric organic molecules with very high accuracy.

According to a first aspect, the present invention provides a system for detecting volatile organic compounds derived from a breath sample, the system comprising (a) an apparatus comprising an array of chemically sensitive sensors of single walled carbon nanotubes coated with an organic coating, wherein the organic coating comprises oligomers or polymers that are modified with at least one polar functional group; and (b) a processing unit comprising a learning and pattern recognition analyzer wherein the learning and pattern recognition analyzer receives sensor output signals and compares them to stored data.

In one embodiment, the system of the present invention further comprises a breath collector wherein the breath collector comprises at least one of a unit for concentrating breath analytes and a dehumidifying unit.

In another embodiment, the single walled carbon nanotubes are organized in a random network configuration.

In some embodiments, the network of SWCNTs is fabricated by physical manipulation of the nanotubes. In other embodiments, the network of SWCNTs is fabricated by a self-assembly process.

According to various embodiments, the single-walled carbon nanotubes of the present invention have diameters ranging from about 0.6 nanometer (nm) to about 100 nanometers (nm). More preferably, the single-walled carbon nanotubes have diameters ranging from about 0.7 nm to about 50 nm. Even more preferably, the single-walled carbon nanotubes have diameters ranging from about 0.8 nm to about 10 nm. Most preferably, the single-walled carbon nanotubes of the present invention have diameters ranging from about 0.9 nm to about 5 nm.

In some embodiments, the single-walled carbon nanotubes of the present invention have lengths ranging from about 50 nanometers (nm) to about 10 millimeters (mm). More preferably, the single-walled carbon nanotubes have lengths ranging from about 250 nm to about 1 mm. Even more preferably, the single-walled carbon nanotubes have lengths ranging from about 0.5 micrometer ($\mu$m) to about 100 micrometers ($\mu$m). Most preferably, the single-walled carbon nanotubes of the present invention have lengths ranging from about 1 $\mu$m to about 50 $\mu$m.

According to certain embodiments, the organic coating of the single walled carbon nanotubes comprises a monolayer or multilayers of organic compounds which form a thin film having thickness in the range of about 20 nanometers (nm) to about 10,000 nm.

In particular embodiments, the organic coating of the single walled carbon nanotubes used in the system of the present invention comprises polymers selected from the group consisting of nafion, polyethyleneimine, methylamine dehydrogenase, poly(aniline-boronic acid), amine-terminated poly(amido amine)dendrimers, poly(4-vinylpyridine), poly(ethylene oxide), poly(methyl vinyl ether-co-maleic anhydride), poly(ethylene-co-vinyl acetate), poly(ethylene glycol), poly(vinyl butyral), polycarbonate, poly(4-vinyl phenol), polycaprolactone, poly-(fluorostyrene), poly(maleic anhydride)-co-poly(methylvinyl ether), and combinations thereof. Each possibility represents a separate embodiment of the invention.

According to other particular embodiments, the organic coating of the single walled carbon nanotubes used in the system of the present invention comprises crosslinked polymers selected from the group consisting of cross-reactive carboxylic acid substituted poly(thiophene), cross-linked dendrimerics of 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone and 1-[4-(4-dimethylaminophenylazo)-3-[3,5-bis[3,5-bis[3,5-bis(2-propene-1-oxy)benzyloxy]benzyloxy]benzyloxy]phenyl]-2,2,2 trifluoro-ethanone, cross-linked poly(p-phenyleneethynylene) containing osmium(II) complex and aldehyde groups, and combinations thereof. Each possibility represents a separate embodiment of the invention.

In specific embodiments, the organic coating of the single walled carbon nanotubes used in the system of the present invention comprises cyclodextrins selected from the group consisting of α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-$6^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxymethylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the invention.

According to some embodiments, the array of chemically sensitive sensors comprises between 2 to 1000 sensors, more preferably between 2 to 500 sensors, even more preferably between 2 to 250 sensors, and most preferably between 2 to 125 sensors in an array.

According to particular embodiments, the array of chemically sensitive sensors further comprises metal nanoparticles capped with an organic coating.

In various embodiments, the metal nanoparticles are selected from Au, Ag, Ni, Co, Pt, Pd, Cu, and Al nanoparticles. Each possibility represents a separate embodiment of the invention.

In other embodiments, the metal nanoparticles are capped with a monolayer or multilayers of organic compounds, wherein the organic compounds are selected from the group consisting of alkylthiols, arylthiols, alkylarylthiols, alkylthiolates, ω-functionalized alkylthiolates, arenethiolates, (γ-mercaptopropyl)tri-methyloxysilane, and combinations and derivatives thereof. Each possibility represents a separate embodiment of the invention.

According to certain embodiments, the system of the present invention comprises a processing unit comprising a learning and pattern recognition analyzer, which receives sensor output signals and compares them to stored data. The learning and pattern recognition analyzer utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention.

In an exemplary embodiment, the algorithm used for processing the data is principal component analysis (PCA).

According to a second aspect, the present invention provides a method for diagnosing renal failure from a breath sample of a subject, comprising: (a) providing a system comprising an apparatus comprising an array of chemically sensitive sensors of single walled carbon nanotubes coated with an organic coating, wherein the organic coating comprises non-polar organic molecules or organic molecules that are modified with at least one polar functional group, and a processing unit comprising a learning and pattern recognition analyzer wherein the learning and pattern recognition analyzer receives sensor output signals from the apparatus and compares them to stored data, (b) exposing the sensor array of the apparatus to the sample, and (c) using pattern recognition algorithms to determine the presence of volatile organic compounds in the sample indicative of renal failure.

In certain embodiments, the detection of volatile organic compounds indicative of renal failure includes measuring a change in any one or more of conductivity, resistance, impedance, capacitance, inductance, or optical properties of the sensors upon exposure to VOCs to be detected. In additional embodiments, the detection of volatile organic compounds comprises the use of spectroscopic ellipsometry.

According to certain embodiments, the present invention provides a method for diagnosing renal failure selected from the group consisting of acute renal failure, chronic renal failure, end stage renal failure, tubular interstitial disease and glomerulonephritis. Each possibility represents a separate embodiment of the invention.

According to other embodiments, the present invention provides a method for diagnosing renal cancer.

In certain embodiments, the organic coating of the single walled carbon nanotubes used for the methods of the present invention comprises polymers selected from the group consisting of nafion, polyethyleneimine, methylamine dehydrogenase, poly(aniline-boronic acid), amine-terminated poly(amido amine)dendrimers, poly(4-vinylpyridine), poly(ethylene oxide), polystyrene, poly(methyl vinyl ether-co-maleic anhydride), poly(ethylene-co-vinyl acetate), poly(ethylene glycol), poly(vinyl butyral), polycarbonate, poly(4-vinyl phenol), polycaprolactone, poly-(fluorostyrene), poly(styrene-co-isoprene), poly(maleic anhydride)-co-poly(methylvinyl ether), and combinations thereof. Each possibility represents a separate embodiment of the invention.

In particular embodiments, the organic coating of the single walled carbon nanotubes used for the methods of the present invention comprises crosslinked polymers selected from the group consisting of cross-reactive carboxylic acid substituted poly(thiophene), cross-linked dendrimerics of 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone and 1-[4-(4-dimethylaminophenylazo)-3-[3,5-bis[3,5-bis[3,5-bis(2-propene-1-oxy)benzyloxy]benzyloxy]benzyloxy]phenyl]-2,2,2 trifluoroethanone, cross-linked poly(p-phenyleneethynylene) containing osmium(II) complex and aldehyde groups, and combinations thereof. Each possibility represents a separate embodiment of the invention.

In other particular embodiments, the organic coating of the single walled carbon nanotubes used for the methods of the present invention comprises cyclodextrins selected from the group consisting of α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-$6^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis(6-O-benzoyl)-α- cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the invention.

In additional embodiments, the organic coating of the single walled carbon nanotubes used for the methods of the present invention comprises organic molecules selected from the group consisting of 2,5-bis(dimethylthiocarbamoyloxy) terephthalic acid diethyl ester, 2,5-bis(dimethyl-thiocarbamoyl-sulfanyl)terephthalic acid diethyl ester, 2,5-dimercaptoterephthalic acid, n-(3-trifluoroethanesulfonyloxypropyl)-anthraquinone-2-carboxamide, 3-methyl 4-(tetraethoxy) thiophene, 3-[n-succinimido(tetra-ethoxy)oxy]-4-methyl thiophene, quinacrine dihydrochloride dehydrate, lauric acid, quinacrine dihydrochloride, dihydrate phthalate, etracosanoic acid, 2,5,6,9,10-hexabromocyclododecane, and combinations thereof. Each possibility represents a separate embodiment of the invention.

In other embodiments, the organic coating of the single walled carbon nanotubes used for the methods of the present invention comprises organic molecules selected from the group consisting of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate(($C_{24}H_{38}O_4$)), 1.2.5.6.9.10-hexabrormo-cyclododecane ($C_{12}H_{18}Br_6$), pentadecane ($C_{15}H_{32}$), and combinations thereof. Each possibility represents a separate embodiment of the invention.

In additional embodiments, the organic coating of the single walled carbon nanotubes used for the methods of the present invention comprises hexa-peri-hexabenzocoronene (HBC) molecules, which are unsubstituted or substituted by any one of 2-ethyl-hexyl (HBC-$C_{6,2}$), 2-hexyldecane (HBC-$C_{10,6}$), 2-decyl tetradecane (HBC-$C_{14,10}$), and dodecane (HBC-$C_{12}$). Each possibility represents a separate embodiment of the invention.

In certain embodiments, the method for diagnosing renal failure in a subject presented herein further comprises the step of increasing breath analyte concentrations using a breath collector, wherein the breath collector comprises at least one of a unit for concentrating breath analytes and a dehumidifying unit.

In some embodiments, the method of the present invention provides the detection of a single analyte breath biomarker (VOC). In other embodiments, the system of the present invention provides the detection of a plurality of breath biomarkers.

In various embodiments, the method of the present invention provides the detection of polar breath biomarkers.

In specific embodiments, the method of the present invention provides the detection of breath biomarkers selected from the group consisting of dimethylamine, trimethylamine, isopalmitate, isopropyl palmitate, isothiocyanato-cyclohexane, 5-methyl-2-(1-methylethyl)-cyclohexanone, nonanal, and 6-nitro-2-picoline. Each possibility represents a separate embodiment of the invention. As contemplated herein, detection of one or more of said analytes in the breath of a subject is indicative of renal failure.

In other embodiments, the method of the present invention enables the detection of different patterns of mixtures of volatile organic compounds wherein the volatile organic compounds are selected from the group consisting of 3-ethyl hexane, undecane, 5,7-dimethyl undecane, 2-methyl undecane, decane, 4,6-dimethyl-dodecane, heptadecane, hexadecane, 4,8-dimethyl-undecane and 3-methyl-4-nonane. Each possibility represents a separate embodiment of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention relates to apparatus and methods for diagnosing renal dysfunction by the detection of breath volatile organic compounds indicative of renal failure. Particularly, the apparatus comprises a plurality of chemically sensitive sensors of SWCNTs coated with organic molecules in conjunction with learning and pattern recognition algorithms for detecting and identifying volatile organic compounds indicative of renal insufficiency of various etiologies. Further disclosed are methods for detecting early stages of renal failure, including, in particular, acute renal failure and chronic renal failure, the methods being applicable for large-scale screening.

Breath analysis offers several potential advantages. Although exhaled breath is mainly composed of $N_2$, $O_2$, $CO_2$, water vapor and other atmospheric constituents (e.g., argon and the like), many volatile organic compounds (VOCs) which are produced by metabolic processes within the body are found therein.

Mixtures containing unique compositions of metabolites can be used as biomarkers of various medical conditions including tissue inflammation (e.g. asthma), immune responses (e.g. to cancer cells or bacteria), metabolic disorders (e.g. diabetes), digestive processes, liver and kidney dysfunction, cardiac disorders, gum disease as well as other physiological conditions. Moreover, mixtures of VOCs are characteristic of a certain disease and often display different patterns at different stages of the disease.

Figure 1:
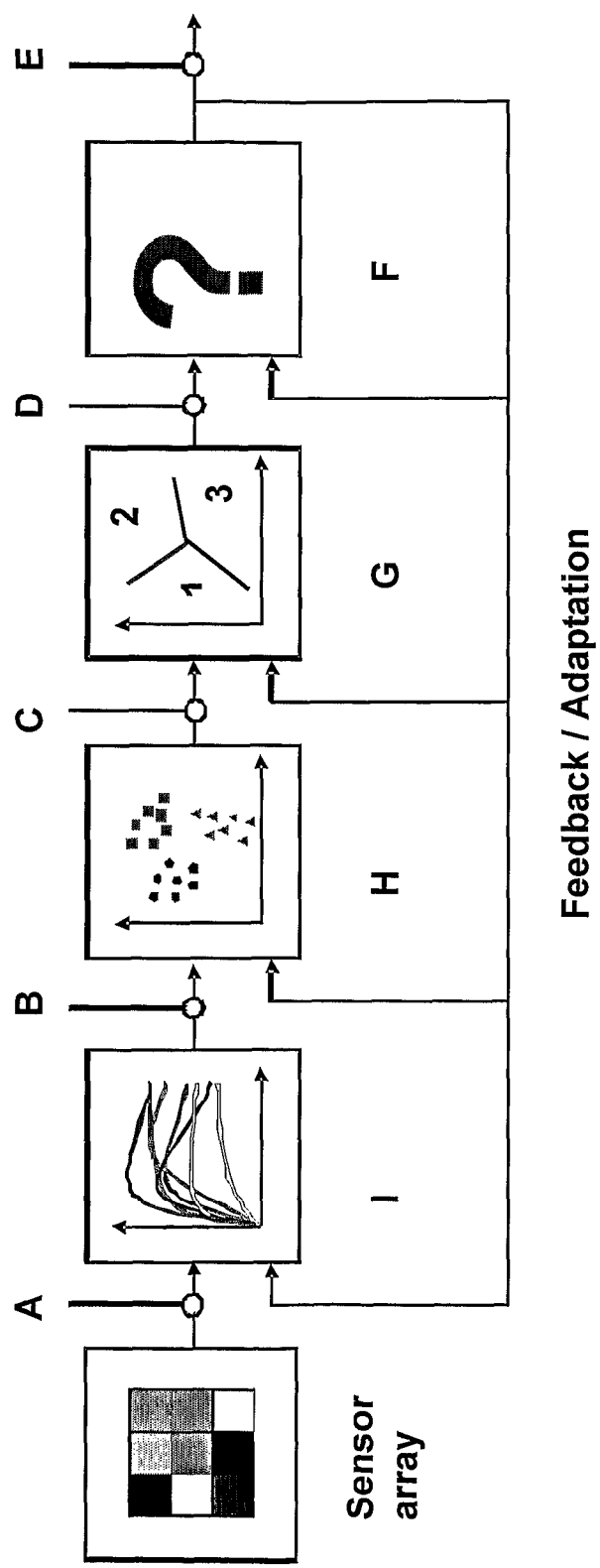
FIG. 1 shows a schematic diagram illustrating the differentiation between odorants using an array of broadly-cross reactive sensors, in which each individual sensor responds to a variety of odorants, in conjugation with pattern recognition algorithms to allow classification. 'A'—raw measurements, 'B'—normalized measurements, 'C'—feature vector, 'D'—odor class (confidence level), 'E'—post processed odor class, 'F'—decision making, 'G'—classification, 'H'—dimensionality reduction, and 'I'—signal preprocessing.

Detection of VOC biomarkers for the diagnosis of medical conditions can be performed using olfactometry systems. These systems, also known as electronic nose devices perform odor detection through the use of an array of cross-reactive sensors in conjunction with pattern recognition methods. In contrast to the hitherto "lock-and-key" based devices, wherein each sensor produces an electronic response from a single analyte, in the electronic nose device each sensor is widely responsive to a variety of odorants. In this architecture, each analyte produces a distinct signature from the array of broadly cross-reactive sensors. This configuration allows to considerably widen the variety of compounds to which a given matrix is sensitive, to increase the degree of component identification and, in specific cases, to perform an analysis of individual components in complex multi-component mixtures. Pattern recognition algorithms can then be applied to the entire set of signals, obtained simultaneously from all the sensors in the array, in order to glean information on the identity, properties and concentration of the vapor exposed to the sensor array (FIG. 1). Various algorithms and computer controlled systems for olfactometry known in the art are disclosed for example in U.S. Pat. Nos. 6,411,905, 6,606,566, 6,609,068, 6,620,109, 6,767,732, 6,820,012, and 6,839,636.

International patent application PCT/IL2009/000532 to one of the inventors of the present invention discloses a system comprising an array of sensors comprising a (semi-)conductive random network of single-walled carbon nanotubes (SWCNTs) coated with small organic molecules in conjunction with learning and pattern recognition algorithms, and methods of used thereof in measuring breath analytes indicative of cancer.

The sensing technology presented herein provides apparatus and methods for diagnosing, detecting, screening and monitoring renal diseases or disorders, especially at the early stages. Recent studies and statistics have indicated that it is extremely important to detect and consequently treat renal disorders as early as possible, before they become fatal. Annual health examinations using conventional methodologies aimed for early detection of glomerulonephritis led to a reduction in the number of instances of progressive glomerulonephritis or alternatively an increase in remission. Thus, additional screening for renal dysfunction in patients having high risk of developing diabetes, hypertension, and metabolic syndromes could result in a decrease in the progression of nephropathy. The technology, according to the principles of the present invention, is relatively inexpensive, portable, and thus particularly suitable for widespread screening.

Early detection of kidney dysfunction can prevent the progression of uremia which is a state of systemic poisoning due to cumulative effects reflecting dysfunction of all organ systems resulting from renal insufficiency. Uremia is characterized by the accumulation of "uremic" toxins, which are retained in the blood. Over 5000 potential toxins associated with renal dysfunction have been identified. These toxins include, inter alia, phenols, indoles, skatoles, pyridine derivatives, polyamines, aliphatic and aromatic amines, hippurate esters, hormones (e.g. prolactin), trace elements (e.g., aluminum, vanadium, arsenic, and zinc), guanidine compounds, serum proteases, and β2-microglobulin.

The present invention overcomes the disadvantages of the hitherto methodologies by providing an apparatus and methods for diagnosing renal failure even at the most early stages of loss of renal functionalities. The present invention thus provides a non-invasive diagnostic technique which enables the detection of breath biomarkers indicative of renal insufficiency. According to the principles of the present invention, the apparatus, system and methods disclosed herein provide the discrimination between different stages of renal failure and the discrimination between chronic renal failure breath samples and acute renal failure breath samples. Within the scope of the present invention is the diagnosis of renal failure of various etiologies.

The analysis of breath samples, according to the principles of the present invention, provides the identification of each breath analyte separately, or alternatively the identification of mixtures comprising a plurality of breath analytes indicative of renal failure. The present invention further provides the reference collection of signatures of biomarker mixtures thus enabling the diagnosis of various stages of loss of renal functionalities from breath samples. The use of pattern recognition algorithms further enables post processing of the output signal in order to eliminate extraneous noise. Certain embodiments include multiplexed assays on a single sensor platform or chip. Other embodiments include the diagnosis of acute renal failure and chronic renal failure at various stages of the disease, particularly early stages.

The present invention provides a system for detecting volatile organic breath analytes, comprising (a) an apparatus comprising an array of chemically sensitive sensors of single walled carbon nanotubes coated with an organic coating wherein the organic coating comprises oligomers or polymers that comprise at least one polar functional moiety; and (b) a processing unit comprising an analyzer comprising learning and pattern recognition algorithms.

The system of the present invention may further comprise a breath collector. The breath collector is used to increase sensing sensitivities either by concentrating the breath analytes to be detected or by dehumidifying the patient's breath prior to analyzing. This allows for increased resolution in discriminating between different breath samples.

Breath pre-concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). The SPME fiber is then inserted directly into the sensing apparatus for desorption and subsequent analysis (Ouyang, et al., *Anal. Bioanal. Chem.*, 2006, 386, 1059-1073; Coelho et al., *J. Chromatography B*, 2007, 853, 1-9).

II. Sorbent Tubes—Sorbent tubes are typically made of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Chemicals are trapped onto the sorbent material throughout the sampling period. This technique was developed by the US National Institute for Occupational Safety and Health (NIOSH).

III. Cryogenic Condensates—Cryogenic condensation is a process that allows recovery of volatile compounds for reuse. The condensation process requires very low temperatures so that the volatile compounds can be condensed. Traditionally, chlorofluorocarbon (CFC) refrigerants have been used to induce condensation. Currently, liquid nitrogen is used in the cryogenic (less than -160° C.) condensation process.

A dehumidifier that is within the scope of the present invention includes, but is not limited to, I. A device which draws moist air over cold refrigerated coils—using this approach, the air moisture condenses into droplets as it passes through cold refrigerated coils into a container. "Dried" air is then brought to its original temperature and returned to the sensing apparatus.

II. Silica Gel—is an amorphous form of silicon dioxide, which is synthetically produced in the form of hard irregular granules or beads. A microporous structure of interlocking cavities gives a very high surface area (800 square meters per gram). This unique structure renders the silica gel as a high capacity desiccant. Water molecules adhere to the surface of the silica gel due to its low vapor pressure as compared to the surrounding air. When pressure equilibrium is reached, the adsorption ceases. Thus, the higher the humidity of the surrounding air, the greater the amount of water that is adsorbed before equilibrium is reached. Silica gel is advantageous as a drying substance since the process of drying requires no chemical reaction and no by products or side effects.

III. Activated carbon—is formed by processing charcoal to an extremely porous carbon substance. Due to its high degree of microporosity the activated carbon possesses a very large surface area available for chemical reactions. Sufficient activation may be obtained solely from the high surface area, though further chemical treatments often enhance the adsorbing properties of the material.

IV. Desiccant Molecular Sieves—are synthetically produced, highly porous crystalline metal-alumino silicates. They are classified by the many internal cavities of precise diameters, namely, 3 Å, 4 Å, 5 Å, and 10 Å. Adsorption occurs only when molecules to be adsorbed have smaller diameters than the cavity openings. Molecules of high polarity are better adsorbed into the molecular sieves. Molecular sieves adsorb water molecules and other contaminants from liquids and gases down to very low levels of concentrations, often to 1 ppm.

According to one embodiment, the single-walled carbon nanotubes (SWCNTs) of the present invention are arranged in a random network configuration. In some embodiments, the network of SWCNTs can be fabricated by physical manipulation or in a self-assembly process. The term "self-assembly" as used herein refers to a process of the organization of molecules without intervening from an outside source. The self-assembly process occurs in a solution/solvent or directly on the solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a silicon wafer in the desired pattern, which may be fashioned using photolithography followed by etching. The silicon wafer having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are now available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods permit the production of carbon nanotube bundles in various shapes.

The term "single walled carbon nanotubes" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by having one of its dimensions (referred to as the length of the nanotube) elongated with respect to the other dimension (which is characterized by its diameter). It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about ranging from about 250 nm to about 1 mm. Even more preferably, the single-walled carbon nanotubes have diameters ranging from about 0.8 nm to about 10 nm and lengths ranging from about 0.5 micrometer (μm) to about 100 μm. Most preferably, the single-walled carbon nanotubes of the present invention have diameters ranging from about 0.9 nm to about 5 nm and lengths ranging from about 1 μm to about 50 μm.

According to certain embodiments, the surface of the single walled carbon nanotube is coated with organic molecules (small molecules, oligomers or polymers). Preferably, these organic molecules form thin films (20-10,000 nm) on the surface of the nanotubes. The coating of the nanotubes, according to the principles of the present invention, can be performed through chemical bonding or alternatively through surface adsorption.

In exemplary embodiments, the coating of the carbon nanotubes can be achieved by any of the methods disclosed herein:

I. Random deposition of organic molecules on solid surfaces. The deposition is performed by drop casting, spin coating, spray coating, and other similar techniques.

II. Langmuir-Blodgett or Langmuir-Schaefer techniques. The substrate is vertically plunged through self-organized/well-ordered 2D film of organic molecules at the air-subphase interface, wherein the latter being subsequently transferred onto it. Multiple plunging of the substrate through the 2D film of the organic molecules at the air-subphase interface, results in the fabrication of a 3D-ordered multilayer organic film.

III. Soft lithographic techniques, including micro-contact printing (mCP), replica molding, micro-molding in capillaries (MIMIC), and micro-transfer molding (mTM). These methods are based on variations of self-assembly and replica molding of organic molecules and polymeric materials, for fabricating films from nanometer-scale to a mesoscopic scale (Whitesides et al., *J. Mater. Chem.*, 1997, 7, 1069-1074).

IV. Various combinations of Langmuir-Blodgett or Langmuir-Schaefer methods with soft lithographic techniques are used to produce patterned Langmuir-Blodgett films of organic molecules and transfer them onto solid substrates.

V. Printing on solid-state or flexible substrates using inject printer that is designated for printed electronics. In this method, a solution containing organic molecules is used as a filling material (or "ink") of the printing head. Few examples on the printing technology are found in Holland et al., *Ink Maker*, 2005, 8, 83; and Rogers, et al., *Nanolitho. Pattern. Tech. Microelect.*, 2005, 373, 76-119.

Coating with organic molecules in the context of the present invention refers to functionalization of the single-walled carbon nanotubes with organic molecules having molecular weight in the range of 50-100,000 grams per mol. The organic molecules can be monomeric, oligomeric or polymeric. The organic molecules can be non-polar, or they can be modified with at least one polar moiety so that their dipole moment values when attached to the single-walled carbon nanotubes are larger than about 1 Debye, more preferably larger than about 1.25 Debye, and most preferably larger than about 1.5 Debye. Particular examples of polar functional groups include, but are not limited to, amine, imine, amide, ammonium, keto, aldehyde, ester, halogen (halo), alcohol, pyridyl, phosphate, thiol, sulfonate, sulfonyl, hydroxyl, carboxylate, carboxyl, and carbonate groups.

Examples of oligomers or polymers suitable for coating the SWCNTs include, but not limited to, nafion (a polymeric perfluorinated sulfonic acid ionomer), polyethyleneimine, poly(aniline-boronic acid), amine-terminated poly(amido amine)dendrimers, poly(4-vinylpyridine), poly(ethylene oxide), poly(methyl vinyl ether-co-maleic anhydride), poly (ethylene-co-vinyl acetate), poly(ethylene glycol), poly(vinyl butyral), polycarbonate, poly(4-vinyl phenol), polycaprolactone, poly-(fluorostyrene), poly(maleic anhydride)-co-poly(methylvinyl ether), and combinations thereof. Each possibility represents a separate embodiment of the invention.

Additional polymers suitable for coating the SWCNTs that are within the scope of the present invention are crosslinked polymers including, but not limited to, cross-reactive carboxylic acid substituted poly(thiophene), cross-linked dendrimerics of 1-[4-(4-dimethylamino-phenylazo)-3-[3,5-bis [3,5-bis[3,5-bis(3-butene-1-oxy)benzyloxy]benzyloxy] benzyloxy]phenyl]-2,2,2 trifluoroethanone and 1-[4-(4-dimethylaminophenylazo)-3-[3,5-bis[3,5-bis[3,5-bis(2-propene-1-oxy)benzyloxy]benzyloxy]benzyloxy]phenyl]-2, 2,2 trifluoro-ethanone, cross-linked poly(p-phenyleneethynylene) containing osmium(II) complex and aldehyde groups, and combinations thereof. Each possibility represents a separate embodiment of the invention.

Without being bound by any theory or mechanism of action, it is contemplated that the crosslinked polymers are capable of producing different and unique adsorptions for a series of structurally similar amine molecules.

Exemplary oligomers suitable for coating the SWCNTs that are within the scope of the present invention are cyclodextrins including, but not limited to, α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-6$^4$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono [6-(o-amino-phenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the invention.

According to the principles of the present invention, the sensor array may further comprise nanoparticles comprising conductive metal cores which are capped with an organic coating. Suitable non-limiting examples of conductive metal cores include, but are not limited to, Au, Ag, Ni, Co, Pt, Pd, Cu, and Al nanoparticles. Each possibility represents a separate embodiment of the invention.

In one embodiment, the coating of the conductive nanoparticle cores comprises a monolayer or multilayers of organic compounds, wherein the organic compounds can be small molecules, monomers, oligomers or polymers. Suitable organic compounds include, but are not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkylthiolates, arenethiolates, and (γ-mercaptopropyl)tri-methyloxysilane. Each possibility represents a separate embodiment of the invention. Other exemplary organic compounds suitable for coating the conductive nanoparticle cores include, but are not limited to, dialkyl sulfides, diaryl sulfides, alkylaryl sulfides, dialkyl disulfides, diaryl disulfides, alkylaryl disulfides, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkyl sulfites, aryl sulfites, alkylaryl sulfites, alkenyl sulfites, alkynyl sulfites, cycloalkyl sulfites, heterocyclyl sulfites, heteroaryl sulfites, alkyl sulfates, aryl sulfates, alkylaryl sulfates, alkenyl sulfates, alkynyl sulfates, cycloalkyl sulfates, heterocyclyl sulfates, heteroaryl sulfates, and the like. Each possibility represents a separate embodiment of the invention.

The term "alkyl" as used herein refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In yet another embodiment, the alkyl group has 3-24 carbons designated here as $C_3$-$C_{24}$-alkyl.

The term "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like.

The term "alkenyl" as used herein refers to an aliphatic hydrocarbon group containing a carbon-carbon double bond including straight-chain, branched-chain and cyclic alkenyl groups. In one embodiment, the alkenyl group has 2-8 carbon atoms. In another embodiment, the alkenyl group has 2-4 carbon atoms in the chain. Exemplary alkenyl groups include ethenyl, propenyl, n-butenyl, i-butenyl, 3-methylbut-2-enyl, n-pentenyl, heptenyl, octenyl, cyclohexyl-butenyl and decenyl.

The term "alkynyl" as used herein refers to an aliphatic hydrocarbon group containing a carbon-carbon triple bond including straight-chain and branched-chain. In one embodiment, the alkynyl group has 2-8 carbon atoms in the chain. In another embodiment, the alkynyl group has 2-4 carbon atoms in the chain. Exemplary alkynyl groups include ethynyl, propynyl, n-butynyl, 2-butynyl, 3-methylbutynyl, n-pentynyl, heptynyl, octynyl and decynyl.

The term "aryl" as used herein refers to an aromatic monocyclic or multicyclic ring system. In one embodiment, the aryl group has 6-10 carbon atoms. The aryl is optionally substituted at least one "ring system substituents" and combinations thereof, and are as defined herein. Exemplary aryl groups include phenyl or naphthyl.

The term "heteroaryl" as used herein refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like.

The terms "heterocyclic ring" or "heterocyclyl" as used herein refer to a five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Exemplary heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein.

The term "ring system substituents" as used herein refers to substituents attached to aromatic or non-aromatic ring systems including, but not limited to, H, halo, $(C_1$-$C_8)$alkyl, $(C_2$-$C_8)$alkenyl, $(C_2$-$C_8)$alkynyl, $(C_6$-$C_{10})$aryl, $(C_5$-$C_{10})$heteroaryl, —CN, —CF$_3$, —NO$_2$, —OH, $(C_1$-$C_8)$alkoxy, —O(CH$_2$)$_n$NRR', —OC(O)R, —OC(O)NRR', —O(CH$_2$)$_n$OR, —CH$_2$OR, —NRR', —C(O)NRR', —C(O)OR and —C(O)R, wherein R and R' are H, alkyl, cycloalkyl, aralkyl, alkaryl, aryl and the like.

The diversity of functionalities and branching provides discrimination between the responses to analytes having subtle differences in molecular structures. Encompassed within the scope of the present invention are SWCNTs which are coated with functionalized organic molecules wherein the functional groups are tailor-made to allow for specific identification of compounds selected from vapors of volatile organic compounds. The technology of the present invention provides fine tuning of the apparatus through modifying the functional groups attached to the sensors to high density functionalities which allow better signal/noise ratios. Tailoring of the functional groups provide sensitive as well as selective responses to breath analytes.

According to additional embodiments, the array of sensors comprises a plurality of sensors between 2 to 1000 sensors, more preferably between 2 to 500 sensors, even more preferably between 2 to 250 sensors, and most preferably between 2 to 125 sensors in an array.

The sensors of the present invention can be configured as any one of the various types of electronic devices, including, but not limited to, capacitive sensors, resistive sensors, impedance sensors, field effect transistor sensors, and the like, or combinations thereof. Each possibility represents a separate embodiment of the invention. Sensors based on carbon nanotubes provide unique electrical characteristics. Moreover, carbon nanotubes are particularly sensitive to environmental changes thus modulating the surface energies. These characteristics render them advantageous for detecting breath analytes.

According to yet other embodiments, the present invention provides apparatus fabricated from random networks of SWCNTs. The random networks can be prepared using various techniques including, but not limited to, chemical vapor deposition (CVD) and traditional lithography, solvent suspension deposition, vacuum deposition, and the like. Within the scope of the present invention are arrays of devices fabricated on a single chip for multiplex and multiparametric applications.

In certain embodiments, the random network of carbon nanotubes is at least partially in contact with one or more conducting elements. The conducting elements may include a source and a drain electrode separated from one another by a source-drain gap. In other embodiments, the network of carbon nanotubes comprises nanotubes having a characteristic length substantially smaller than the source-drain gap, so that the nanotubes comprising the network substantially contact at most, only one of the source and drain electrodes. In yet other embodiments, the characteristic length is substantially larger than the source-drain gap, so that a substantial portion of the nanotubes comprising the network, contact both the source and the drain electrodes.

The system disclosed herein may further comprise a gate electrode wherein the sensor signal may be indicative of a certain property of the nanostructure under the influence of a gate voltage. Alternatively, the sensor signal may be indicative of a capacitance property of the nanostructure.

The sensor signal may be induced, according to the principles of the present invention by a change in any one or more of conductivity, resistance, impedance, capacitance, inductance, or optical properties of the sensors upon exposure to volatile organic compounds. Changes in the optical properties of the sensor network can be measured using e.g., spectroscopic ellipsometry. This technique measures the change in polarization upon reflection of polarized light from a surface. Without being bound by any theory or mechanism of action, the adsorption of analyte molecules induces changes in thickness of the random network SWCNTs. The change in thickness or roughness induces changes in polarization which can be recorded by the spectroscopic ellipsometry technique. The signal obtained is subsequently conveyed to a learning and pattern recognition analyzer to generate a result. In this manner no electrical contacts are required.

According to another embodiment, the present invention further provides a processing unit comprising a learning and pattern recognition analyzer, wherein the learning and pattern recognition analyzer receives sensor output signals and analyses them by various pattern analysis algorithms to produce an output signature. By comparing an unknown signature with a database of stored or known signatures, volatile organic compounds can be identified. The analyzer utilizes learning and pattern recognition algorithms comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the invention. In an exemplary embodiment, the algorithm used for processing the data is principal component analysis (PCA).

Additional algorithms suitable for identifying patterns of VOCs and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the invention. In some embodiments, the Fisher linear discriminant analysis (FLDA) and canonical discriminant analysis (CDA) and combinations thereof are used to compare the output signature and the available data from the database. After analysis is completed, the resulting information can be displayed on a display or transmitted to a host computer.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

In operation, when a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

In particular embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Specifically, PCA compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a proportional constant. Another relationship between matrices is that they share principal components in common, but their eigenvalues differ. The mathematical technique used in PCA is called eigen analysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

The present invention further provides a method for diagnosing renal failure from a breath sample of a subject, comprising: (a) providing a system comprising an apparatus comprising an array of chemically sensitive sensors of single walled carbon nanotubes coated with non-polar organic molecules or organic molecules, particularly oligomers and polymers that are modified with at least one functional moiety and a processing unit comprising a learning and pattern recognition analyzer wherein the learning and pattern recognition analyzer receives sensor output signals from the apparatus and compares them to stored data, (b) exposing the sensor array of the apparatus to the breath sample of the subject, and (c) analyzing the signal obtained from the sensor array upon exposure to the breath sample using pattern recognition algorithms to detect volatile organic compounds in the sample indicative of renal failure.

Organic coatings that are suitable for coating the SWCNTs in order to provide diagnosis of renal failure include, but are not limited to, 1. Polymers selected from nafion (a polymeric perfluorinated sulfonic acid ionomer), polyethyleneimine, poly(aniline-boronic acid), amine-terminated poly(amido amine) dendrimers, poly(4-vinylpyridine), poly(ethylene oxide), polystyrene, poly(methyl vinyl ether-co-maleic anhydride), poly(ethylene-co-vinyl acetate), poly(ethylene glycol), poly(vinyl butyral), polycarbonate, poly(4-vinyl phenol), polycaprolactone, poly-(fluorostyrene), poly(styrene-co-isoprene)

poly(maleic anhydride)-co-poly(methylvinyl ether), and combinations thereof. Each possibility represents a separate embodiment of the invention.

2. Crosslinked polymers selected from cross-reactive carboxylic acid substituted poly(thiophene), cross-linked dendrimerics of 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone and 1-[4-(4-dimethylaminophenylazo)-3-[3,5-bis[3,5-bis[3,5-bis(2-propene-1-oxy)benzyloxy]benzyloxy]benzyloxy]phenyl]-2,2,2 trifluoro-ethanone, cross-linked poly(p-phenyleneethynylene) containing osmium(II) complex and aldehyde groups, and combinations thereof. Each possibility represents a separate embodiment of the invention.

3. Cyclodextrins selected from α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-$6^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono [6-(o-amino-phenyl)imino-6-deoxy]-β-cyclodextrin, mono [6-(p-aminophenyl)imino-6-deoxy]-β-cyclodextrin, mono [6-(α-naphthyl)imino-6-deoxy]-β-cyclodextrin, hexakis(6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof. Each possibility represents a separate embodiment of the invention.

4. Organic molecules selected from 2,5-bis(dimethylthiocarbamoyloxy)terephthalic acid diethyl ester, 2,5-bis(dimethyl-thiocarbainoyl-sulfanyl)terephthalic acid diethyl ester, 2,5-dimercaptoterephthalic acid, n-(3-trifluoroethanesulfonyloxypropyl)-anthraquinone-2-carboxamide, 3-methyl 4-(tetraethoxy)thiophene, 3[n-succinimido(tetra-ethoxy)oxy]-4-methyl thiophene, quinacrine dihydrochloride dehydrate, lauric acid, quinacrine dihydrochloride, dihydrate phthalate, etracosanoic acid, 2,5,6,9,10-hexabromocyclododecane, and combinations thereof. Each possibility represents a separate embodiment of the invention; and 5. Organic molecules selected from propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$), dioctyl phthalate (($C_{24}H_{38}O_4$)), 1.2.5.6.9.10-hexabrormo-cyclododecane ($C_{12}H_{18}Br_6$), pentadecane ($C_{15}H_{32}$), and combinations thereof. Each possibility represents a separate embodiment of the invention.

6. Hexa-peri-hexabenzocoronene (HBC) molecules which are unsubstituted or substituted by any one of 2-ethyl-hexyl (HBC-$C_{6,2}$), 2-hexyl decane (HBC-$C_{10,6}$), 2-decyl tetradecane (HBC-$C_{14,10}$), and dodecane (HBC-$C_{12}$). Each possibility represents a separate embodiment of the invention.

The methods of the present invention enable the detection of a single analyte breath biomarker as well as the detection of a plurality of breath biomarkers and the unique pattern of VOCs which characterizes a particular renal disorder. In certain embodiments, the pattern of VOCs comprises analytes selected from the group consisting of dimethylamine, trimethylamine, isopalmitate, isopropyl palmitate, isothiocyanato-cyclohexane, 5-methyl-2-(1-methylethyl)-cyclohexanone, nonanal, and 6-nitro-2-picoline. Each possibility represents a separate embodiment of the invention.

Other exemplary VOCs which can be detected according to the principles of the present invention include, but are not limited to, 3-ethyl hexane, undecane, 5,7-dimethyl undecane; 2-methyl undecane, decane, 4,6-dimethyl-dodecane, heptadecane, hexadecane, 4,8-dimethyl-undecane and 3-methyl-4-nonane. Each possibility represents a separate embodiment of the invention.

The present invention encompasses the detection of breath biomarkers indicative of a wide variety of renal disorders. The renal failure that can be diagnosed according to the principles of the present invention comprise indications selected from acute renal failure, chronic renal failure, end stage renal failure, tubular interstitial disease and glomerulonephritis. Each possibility represents a separate embodiment of the invention. In other embodiments, the present invention provides a method for diagnosing renal failure which occurs as a result of renal cancer.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The principles of the present invention are demonstrated by means of the following non-limitative examples.

EXAMPLES

Example 1

Rat Model for Chronic Renal Failure (CRF)

The experiments were carried out on Sprague Dawley rats weighing between 290 to 330 g (Harlan Laboratories Ltd., Jerusalem, Israel). The animals were kept in a temperature-controlled room, and were fed with standard rat chow containing 0.5% NaCl and tap water ad libitum. All experiments were performed according to the guidelines of the Technion Committee for Supervision of Animal Experiments (Haifa, Israel).

Figure 2:
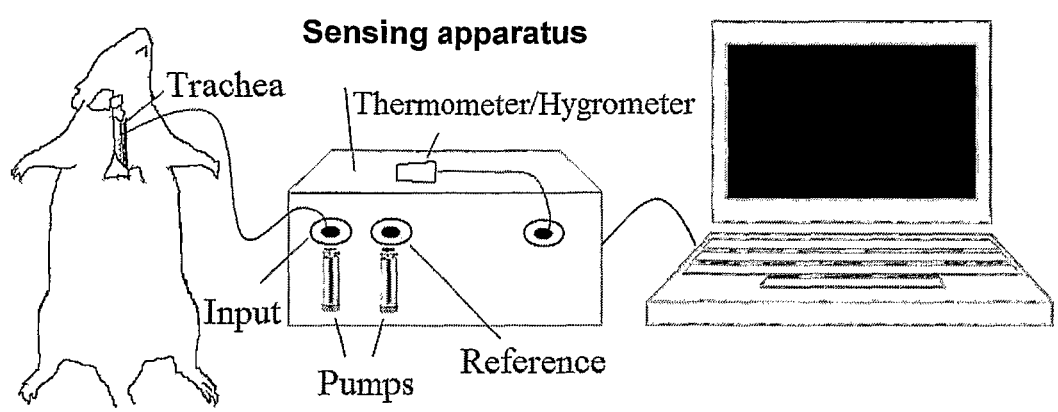
FIG. 2 shows an illustration of the experimental setup.

The surgical procedures for the induction of chronic renal failure of different severities were performed according to known procedures (Mashiach et al., *Nephron*, 80, 458, 1998). In particular, animals were anesthetized by intraperitoneal injection of a Nembutal (40 mg/kg; ip) and placed on a temperature-regulated table (37° C.) to maintain body temperature. A protocol for bilateral nephrectomy which mimics clinical ESRD (CRF stage V) was then performed. Using this protocol, both right and left kidneys were removed and the animals were allowed to recover. Two days later the animals were re-anesthetized and tracheostomy was performed for breath sampling through a period of 2 hours. The experimental setup is shown in FIG. 2. The carotid artery was cannulated for blood collection in order to determine urea, creatinine, and other waste products levels according to classic methodologies.

Figure 3A:
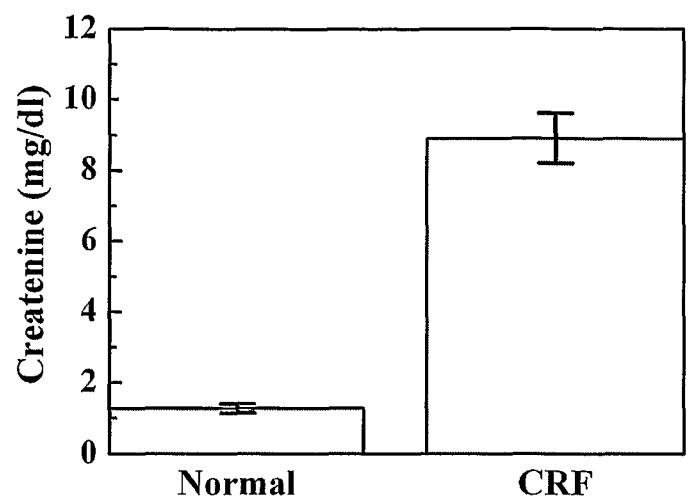
FIGS. 3A-3B show plasma levels of (3A) Creatinine and (3B) Blood urea nitrogen (BUN) in healthy rats (Normal) and in rats following bilateral nephrectomy (CRF).
Figure 3B:
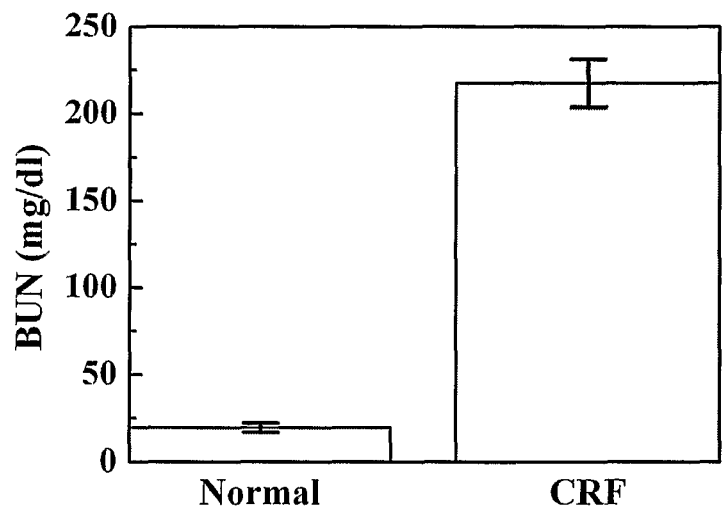

Blood analysis of creatinine and urea levels that was measured using the classic routine method (Rambam Chemical Laboratories) revealed that rats that underwent bilateral nephrectomy displayed remarkable elevation of creatinine (8.73±0.73 vs. 0.42±049. mg %, P<0.001) and BUN (218.0±13.74 vs. 19.8±2.2 mg %, p<0.001; FIGS. 3A and 3B, respectively), thus confirming that the rat model used herein resembles clinical end stage renal disease (ESRD).

Breath samples from "healthy" and "diseased" rats were collected directly from the Trachea, using the on-line approach, where rats breathed directly on the sensor array of the present invention and the diagnosis was obtained in real time. Rats were connected to a tube that was split into an inlet and an outlet, each connected to a one-way valve. The outlet tube was used for connecting the rat to the sensing system for breath analysis while the inlet tube enabled the rat to inhale air from the room. For comparative studies 500-1000 $cm^3$ breath samples were collected in Tedlar bags for GC-MS analysis.

Example 2

GC-MS Analysis of Breath Samples (Rat Model of CRF vs. Healthy)

Breath samples that were collected from "healthy" and "diseased" rats were analyzed using GC-MS combined with solid phase micro-extraction (SPME). The SPME system was used for pre-concentrating the VOCs from breath samples. A manual SPME holder with an extraction fiber of 100 μm Polydimethylsiloxane (PDMS), 65 μm Polydimethylsiloxane-Divinylbenzene (PDMS/DVB), or 75 μm Polydimethylsiloxane-Carboxen (PDMS/Carboxen), all purchased from Sigma-Aldrich was inserted into a Mylar bag. Approximately 100-500 $cm^3$ of each breath sample were concentrated using the SPME system for 2 hours and subsequently delivered to the GC-MS using a manual SPME holder. The extracted fiber in the manual SPME holder was inserted into the GC injector operated using the splitless model. The oven temperature profile was 60° C. and 2 minutes. A capillary column HP-5MS 5% Phenyl Methyl Siloxane (30 m length, 250 μm diameter, 0.25 μm thickness) was used. The column pressure was set to 8.22 psi and the initial flow was 1 mL/min. The VOCs were determined using Automated Mass Spectral Deconvolution and Identification System (AMDIS) software which was developed for spectral extraction and compound identification by GC/MS. Eventually, the molecular structures of the VOCs were determined via the Standard Modular Set.

Figure 4A:
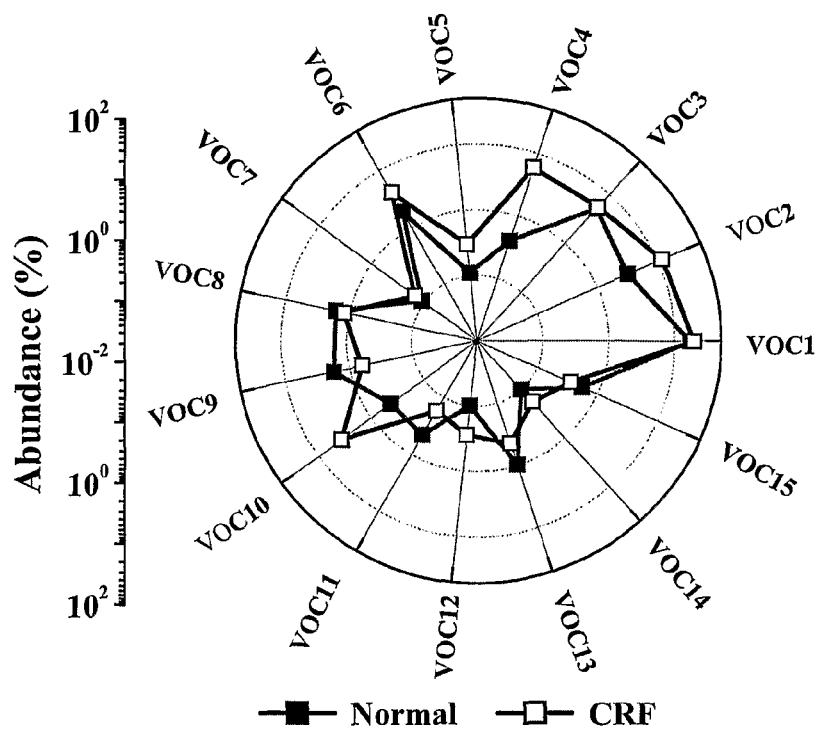
FIGS. 4A-4B show the abundance of volatile organic compounds in breath samples. (4A) VOCs that appear both in "healthy" (full squares) and "diseased" (CRF; empty squares) states, and (4B) VOCs that appear in "diseased" but not in "healthy" states. VOCs' abbreviations are presented in Table 1.
Figure 4B:
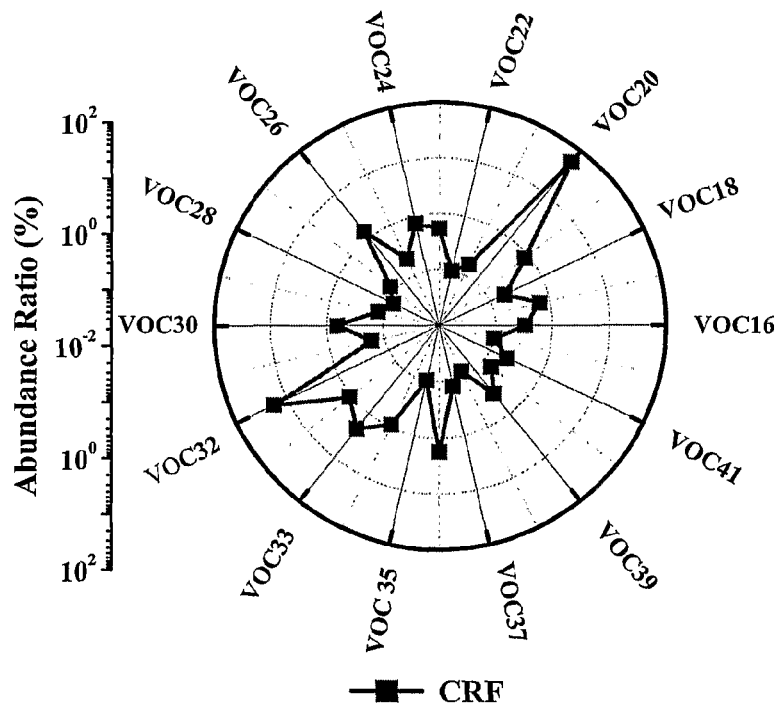

GC-MS of breath samples identified 100-180 different VOCs that were either synthesized or catabolized in at least one of "healthy" or "diseased" states. In order to narrow the number of VOCs, forward stepwise discriminant analysis was performed identifying 15 VOCs that appeared in all samples of "healthy" and "diseased" states with >90% confidentiality. As shown in FIG. 4A and Table 1, the most common VOCs that were obtained included phenol, oxalic acid, and derivatives of $C_3$-$C_{11}$ alkanes. Excluding 4-methyl-octane (VOC9), 3,5-dimethyl-octane (VOC11), and propane (VOC13), all other VOCs appeared to be elevated in instances of chronic renal failure ("diseased" states; empty squares), as compared to "healthy" states (controls; full squares). Additional forward stepwise discriminant analysis revealed 27 VOCs that appeared in "diseased" states but not in "healthy" states (FIG. 4B). These compounds could be classified into derivatives of amines, alkenes, acids, and alcohols, wherein dimethylamine (VOC20) and trimethylamine (VOC32) exhibited the highest concentrations.

TABLE 1

Abbreviations of volatile compounds detected by the GC-MS analysis for "healthy" and/or "diseases" samples. The abundance of compounds in breath samples is shown in FIGS. 4A-4B.

| VOC # | Chemical |
|---|---|
| 1 | Phenol |
| 2 | Decane |
| 3 | N,N-dimethyl acetamide |
| 4 | 3-Ethyl-hexane |
| 5 | Undecane |
| 6 | 4-Ethyl-5-methyl-nonane |
| 7 | 2-Bromo-heptane |
| 8 | 2,4-Dimethyl-heptane |
| 9 | 4-Methyl-octane |
| 10 | 2-Methyl-undecane |
| 11 | 3,5-Dimethyl-octane |
| 12 | 5,7-Dimethyl-undecane |
| 13 | Propane |
| 14 | 3-Methyl-4-nonene |
| 15 | Oxalic acid |
| 16 | Ethyl alcohol |
| 17 | Acetic acid |
| 18 | Isopropyl alcohol |
| 19 | Acetone |
| 20 | Dimethylamine |
| 21 | Dibutyl phthalate |
| 22 | Diphenyl ether |
| 23 | Ethyl-oxirane |
| 24 | Toluene |
| 25 | 2-Methyl-1-propene |
| 26 | Isopropyl palmitate |
| 27 | Acetic acid |
| 28 | 2,3,3-Trimethyl-pentane |
| 29 | 2-Ethyl hexanol |
| 30 | 2-Propyl-1-heptanol |
| 31 | 1,2-Benzenedicarboxylic acid |
| 32 | Trimethylamine |
| 33 | 6-Nitro-2-picoline |
| 34 | 6-undecylamine |
| 35 | Phenethyl-benzonitrile |
| 36 | 2H-Pyran |
| 37 | N-Morpholinomethyl-isopropyl-sulfide |
| 38 | N-Dimethylaminomethyl |
| 39 | 9-Decyl-9-borabicyclononane |
| 40 | 2-Phenylacenaphthenopyrrole |
| 41 | Cyclobutane |
| 42 | Sclareoloxide |

Example 3

Comparative Studies: Analysis of Exhaled vs. Simulated Breath Samples

Exhaled breath samples were analyzed using an array of 32 organic compounds/single walled carbon nanotube composite sensors, in conjugation with acquisition system, and a processor. The organic compounds that were used in this set of experiments were: propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$)+dioctyl phthalate(($C_{24}H_{38}O_4$) (3:1 w/w), tetracosanoic acid ($C_{24}H_{48}P_2$)+dioctyl phthalate(($C_{24}H_{38}O_4$) (3:1 w/w), 1.2.5.6.9.10-hexabrormo-cyclododecane ($C_{12}H_{18}Br_6$)+dioctyl phthalate($C_{24}H_{38}O_4$) (3:1 w/w), pentadecane ($C_{15}H_{32}$)+dioctyl phthalate ($C_{24}H_{38}O_4$) (3:1 w/w), poly(4-vinylpyridine), poly(ethylene oxide), quinacrine dihydrochloride dehydrate, polystyrene, lauric acid/dioctyl phthalate, tetracosane/dioctyl phthalate, poly(methyl vinyl ether-co-maleic anhydride), tetracosanoic acid, quinacrine dihydrochloride, poly(ethylene-co-vinyl acetate), dihydrate/dioctyl phthalate, poly(ethylene glycol), etracosanoic acid/dioctyl phthalate, poly(vinyl butyral), 2,5,6,9,10-hexabromocyclododecane/dioctyl phthalate, polycarbonate, poly(4-vinyl phenol), quinacrine dihydrochloride, dihydrate/dioctyl phthalate, polycaprolactone, poly-(fluorostyrene), and poly(styrene-co-isoprene).

The sampling system sequentially delivered ambient air and sample vapors to the sensors. The processor and pattern recognition software collected and analyzed the responses of the sensors to different vapors. Each sensor in the sensor array produced a reversible response wherein the electrical resistance varied upon exposure to a vapor analyte. Consequently, a pattern of changes in resistance was obtained from the sensor array. A minimum of five analyses was performed on exhaled breath for each sample.

A computer-controlled automated flow system delivered pulses of simulated biomarker(s) of VOCs to the detectors. Main parameters that were controlled included the fraction of the biomarker(s), and vapor pressure(s). Oil-free air, obtained from a compressed air source was used as a carrying gas for the VOC biomarkers. In a typical experiment, signals were collected for duration of 3 minutes of vapor analyte exposure. Prior to each measurement, 2 minutes of clean air was introduced in order to purge the system. Similarly, 2 minutes of clean air was further introduced after each measurement. Data analysis of the signals, collected from all sensors in the sensor array, was performed using standard principal component and cluster analysis.

Example 4

Discrimination Between Exhaled Breaths of "Healthy" vs. "Diseased" (CRF) Rats

Figure 5:
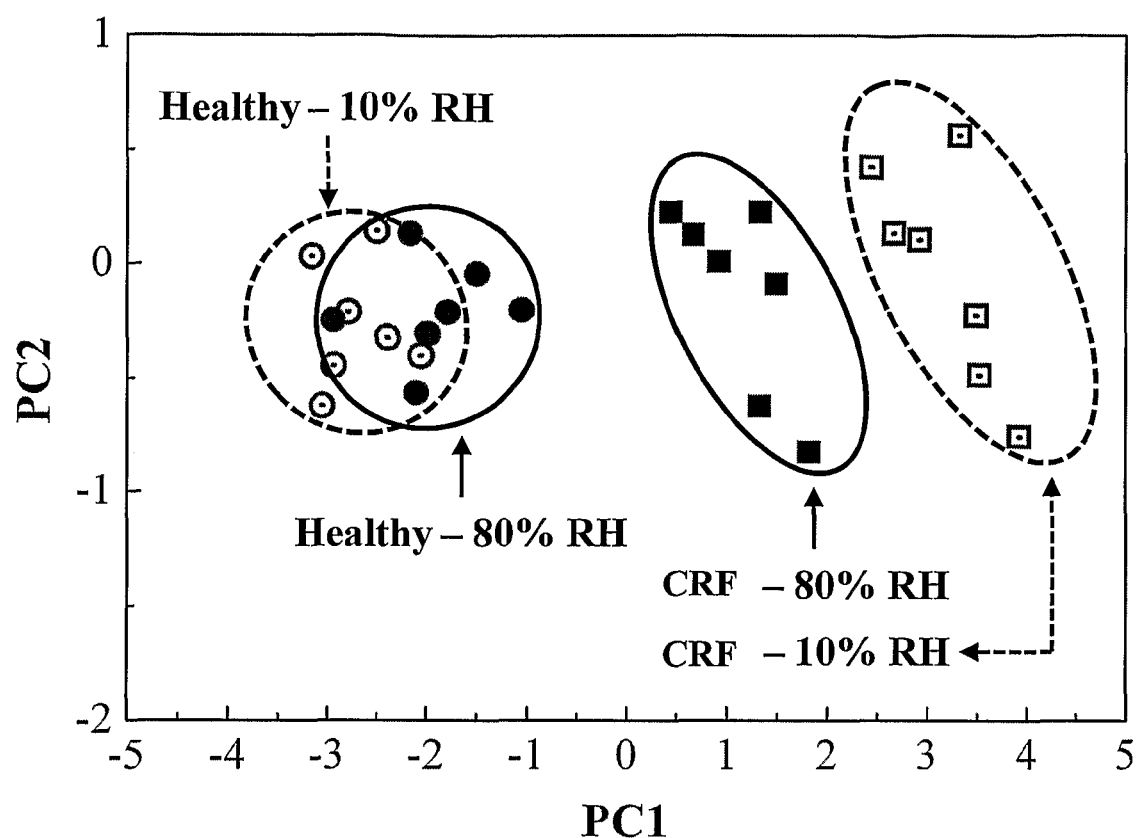
FIG. 5 shows a principal component analysis plot of $\Delta R/R_b$ response of an array of 32 sensors of the present invention upon exposure to breath samples of healthy and diseased rats (CRF) at ~80% relative humidity (RH) and after dehumidifying to 10% relative humidity (RH).

To discriminate between "healthy" and "diseased" breath samples, the normalized sensor signals were analyzed using principal component analysis (PCA). FIG. 5 shows the $1^{st}$ and $2^{nd}$ principal components, which account for >92% of the variance in the data, for each subject. The $1^{st}$ to $3^{rd}$ principal components account for 94% of the variance in the data. In samples having 80% relative humidity (RH), healthy controls formed a discrete cluster (full circles), well separated from all diseased breath samples (full squares). In samples that were dehumidified to include only 10% relative humidity, an even better discrimination was obtained (empty circles for healthy controls vs. empty squares for diseased samples). The overlapping area between the clusters of healthy breath at ~80% and ~10% RH indicate that the effect of humidity on healthy breath is relatively small, as compared to diseased breath, where no overlapping area was observed between the clusters at ~80% RH and ~10% RH.

Example 5

Discrimination Between Simulated "Healthy" and "Diseased" (CRF) Breath Samples

In order to validate the efficacy of the system of the present invention in discriminating healthy and diseased breath samples, mixtures of volatile organic compounds that simulate chronic renal failure (CRF) and healthy states were prepared and subsequently used as analyte mixtures to be detected. Using this approach, the signature of each individual CRF volatile biomarker on the developed array of sensors can be determined. Furthermore, the correlation between sensor sensitivity and specificity to an individual VOC biomarkers and its presence in a pattern (or mixture) of other compounds can be measured accurately. This approach further provides the iterative feedback on sensors viability without the intervention of (disruptive) parameters including, for example, the diet of the patient, metabolic state, genetics, etc.

Figure 6:
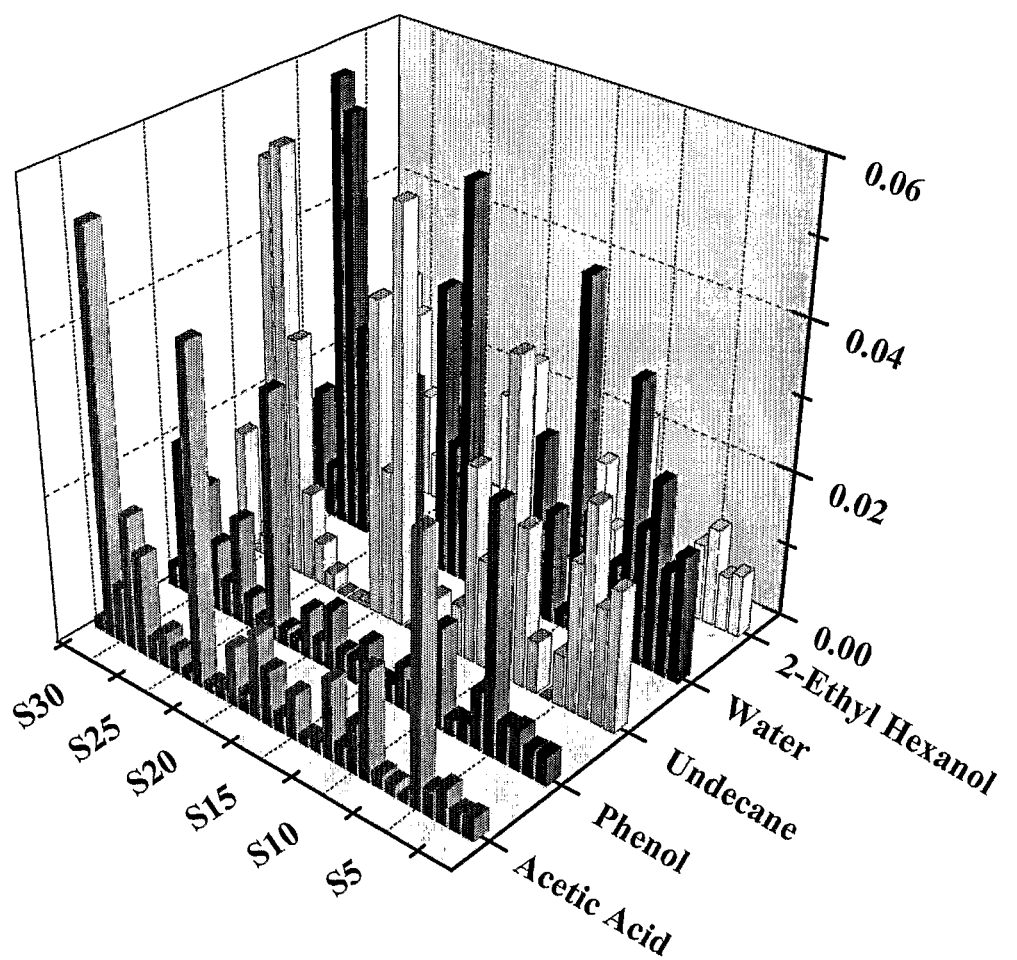
FIG. 6 shows a diagram of the response patterns for representative VOC biomarkers.

The response ($\Delta R/R_b$, where $R_b$ is the baseline resistance of the sensor in the absence of analyte, and $\Delta R$ is the baseline-corrected steady-state change in resistance upon exposure of the sensor to analyte) of the sensor array to different CRF biomarkers at concentrations of 0.5-100 ppm was first examined. All the sensors showed increased resistance upon exposure to a certain VOC biomarker (FIG. 6). Without being bound by any theory or mechanism of action, these changes could be attributed to the swelling of the organic coating/SWCNT composites upon adsorption of biomarkers. In particular, each VOC biomarker produced a unique signal response pattern. Most importantly, the response obtained from the sensor array produced well defined discrimination between individual VOC biomarkers and water.

Mixtures of representative VOCs that were presented in most CRF samples at the highest concentration levels according to the GC-MS measurements were prepared. These mixtures containing phenol, 2-ethyl hexanol, acetic acid, and undecane simulate CRF breath patterns. The system comprising an array of 32 organic coating/single walled carbon nanotube composite sensors was then exposed to the VOC mixtures via a homemade system. Additionally, simulated breath patterns were prepared in 80±1% relative humidity to simulate the background water vapor content in exhaled breath. Simulated "healthy" breath patterns were prepared as controls. Specifically, a mixture of 44.3% phenol, 0.42% 2-ethyl hexanol, 1.62% acetic acid, and 2.92% undecane with 80±1% (or 10±1%) RH, 16±1% $O_2$, 5±1% $CO_2$, and 1.0±0.2 ppm CO was used to simulate "diseased" breath; a mixture of 36.66% phenol and 0.42% 2-ethyl hexanol with 80±1% (or 10±1%) RH, 16±1% $O_2$, 5±1% $CO_2$, and 1.0±0.2 ppm CO was used to simulate "healthy" breath.

Analyte mixtures produced a rapid response which was fully reversible upon switching back to zero vapor analyte (purified, dry air). Furthermore, the sensor array produced a response to a wide variety of concentrations of analytes with satisfying signal-to-noise ratios. Multiple exposures to each mixture were performed and data were obtained for the array of sensors. As could be observed in FIGS. 7A-7B, the cluster of simulated healthy controls was fully separated from the cluster of simulated CRF breath, at both 80% RH and 10% RH with no overlapping area between the principle components of these categories. It is noteworthy that the lower the RH the better the separation (or discrimination) between the healthy and CRF clusters.

Example 6

Principle Component Analysis of Breath Samples

Figure 7A:
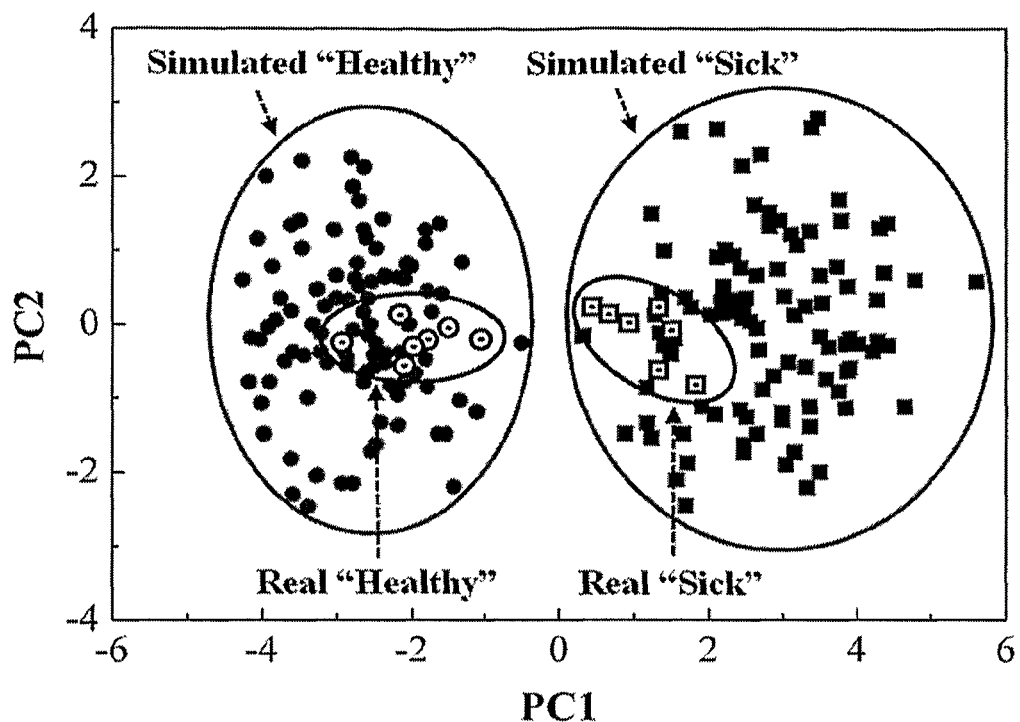
FIGS. 7A-7B show real (empty) and simulated (full) "healthy" (circles) and "diseased" (squares) patterns with (7A) 80% relative humidity and (7B) 10% relative humidity.
Figure 7B:
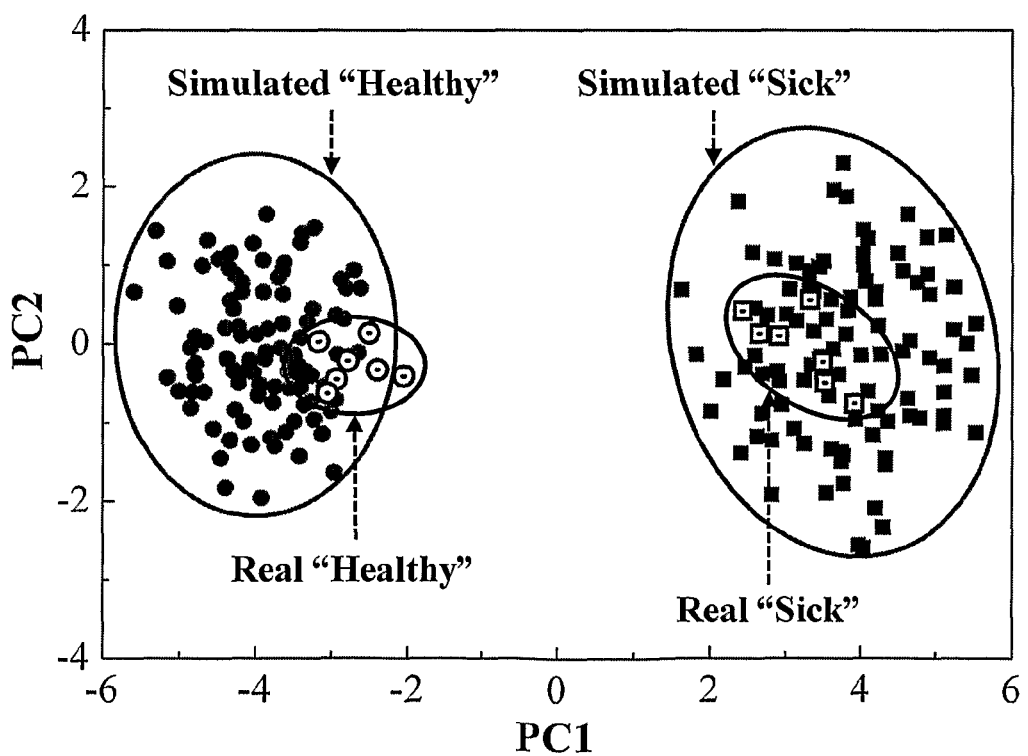

The array of 32 organic coating/single walled carbon nanotube composite sensors was then exposed to the VOC mixtures of real breath samples from healthy vs. diseased (CRF) populations. FIGS. 7A-7B show that the cluster of simulated breath samples was widely distributed as compared to the cluster of real breath samples. Without being bound by any theory or mechanism of action, this could be attributed to the low number of compounds used to produce the required mixtures (4 VOCs for simulating CRF states and 2 VOCs for simulating "healthy" states), as compared to those detected in the real breath (15 VOCs in "healthy" breath and 42 VOCs in "CRF" breath). Furthermore, the principle components also differ between ~80% RH and 10% RH wherein the lower the humidity (i.e., 10% RH vs. 80% RH) the lower the distribution providing better discrimination between samples. Without being bound by any theory or mechanism of action, this observation could be attributed to the screening effect of the water molecules which appear at equivalent concentration levels to that of the targeted VOCs at 80% RH.

The results presented herein clearly demonstrate that through the use of the apparatus, system and methods of the present invention one can obtain clear discrimination between breath samples of patients suffering from chronic renal failure and breath samples from healthy subjects.

Example 7

Rat Model for Acute Renal Failure

Rats were anesthetized with a combination of 87 mg/kg ketamine and 13 mg/kg xylazine through intubation. Acute renal failure was induced in rats #3 and #4 by injection of Cis platin (20 mg/kg intraperitonealy), and in rat #5 by injection of $HgCl_2$ (7.5 mg/kg, intraperitonealy). Both materials are nephrotoxic and are known to induce acute renal failure. Breath samples were collected directly from the intubation a few hours prior to drug administration (baseline) and 2 h (hours), 4 h, 24 h, 48 h, 3 d (days), 4 d and 7 d after drug administration (i.e. induction of acute renal failure). Simultaneously, blood samples were withdrawn from the tail vein at the indicated time points to determine plasma creatinine levels using conventional techniques for comparison. The creatinine values of the examined rats are summarized in Table 2. Rats #1 and #2 were used as control (sham rats), and each baseline value was used as pre AKI reference.

TABLE 2

Creatinine levels in ARF and sham rats at different times

|  | Rat # | Creatinine |
| --- | --- | --- |
| Baseline | 1 | 0.9 |
|  | 2 | 0.8 |
|  | 3 | 0.8 |
|  | 4 | 0.8 |
|  | 5 | 0.9 |
| 2 hrs | 1 | 0.8 |
|  | 2 | 0.8 |
|  | 3 | 0.9 |
|  | 4 | 0.8 |
|  | 5 | 0.8 |
| 4 hrs | 1 | — |
|  | 2 | — |
|  | 3 | 0.7 |
|  | 4 | 0.9 |
|  | 5 | 1.1 |
| 24 hrs | 1 | — |
|  | 2 | — |
|  | 3 | 0.8 |
|  | 4 | 0.8 |
|  | 5 | 1.9 |
| 48 hrs | 1 | 0.8 |
|  | 2 | 0.7 |
|  | 3 | 1.0 |
|  | 4 | 1.0 |
|  | 5 | 2.2 |
| 96 hrs | 1 | 0.8 |
|  | 2 | 0.9 |
|  | 3 | 2.9 |
|  | 4 | 3.3 |
|  | 5 | 1.0 |
| 168 hrs | 1 | 0.6 |
|  | 2 | 0.9 |
|  | 3 | Died |
|  | 4 | 4.7 |
|  | 5 | 0.7 |

Example 8

Sensing of VOCs Indicative of Acute Renal Failure

Breath samples taken from the rats #3 and #4 were analyzed using both SWCNT-based sensor and Gas-Chromatography linked to Mass-spectrometry (GC-MS) in conjugation with Solid Phase Microextraction (SPME; Divinylbenzene/Carboxen/Polydimethylsiloxane). GC-MS results showed over 70 different volatile organic compounds in all breath samples. However, only few of these volatile compounds showed variations that were correlated with the progression of acute renal failure. Accordingly, only volatile compounds that were found in all acute renal failure rats were considered in the analysis. These compounds were found to be in a good correlation with the sensors response. The results of the sensor system of the present invention and of the GC-MS of rat #3 are summarized in FIGS. 8 and 9A-9C, respectively.

Figure 8:
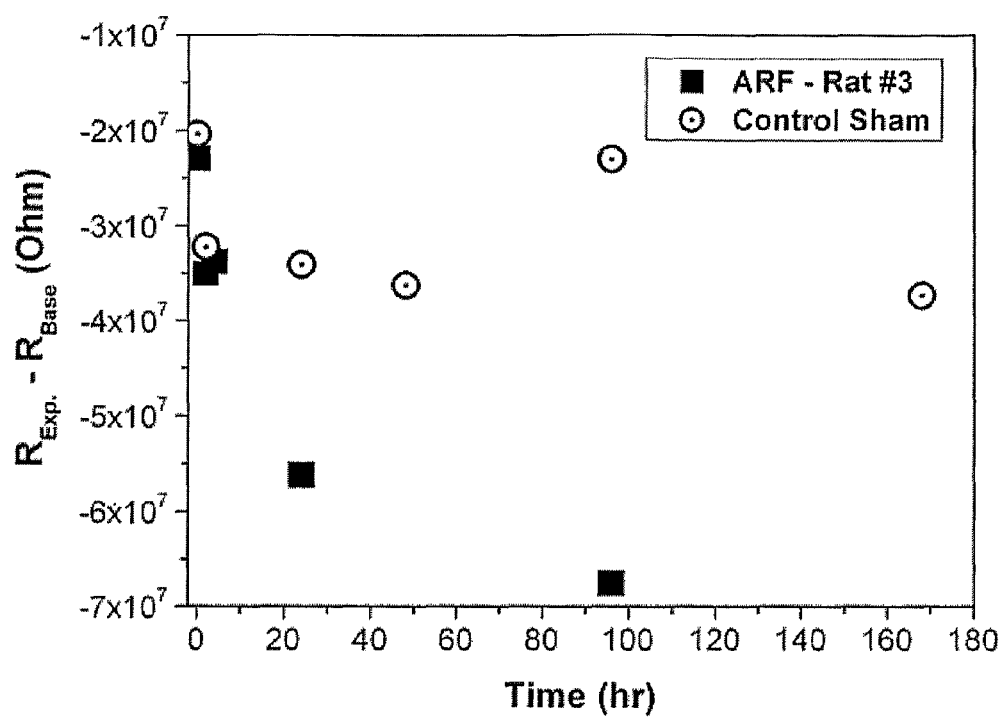
FIG. 8 shows the response of chemiresistive random network of SWCNTs covered with $C_4H_9NO_5$ when exposed to a breath sample of rat #3 (full squares) and control sham (empty circles) at different times.
Figure 9A:
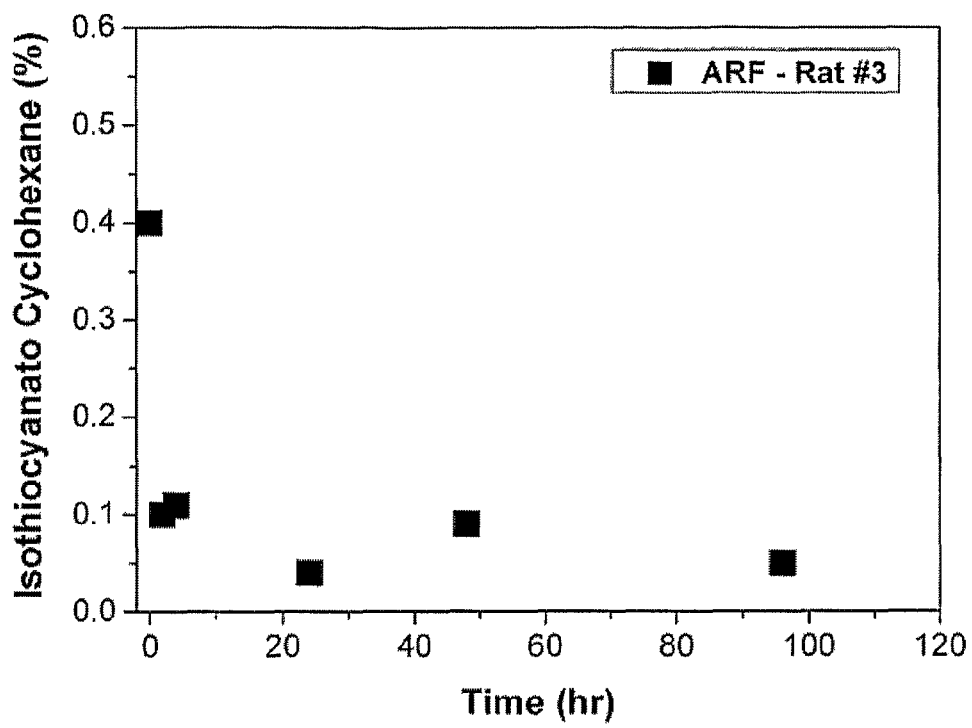
FIGS. 9A-9C show GC-MS abundance of (9A) isothiocyanato cyclohexane (9B) 5-methyl-2-(1-methylethyl)-cyclohexanone, and (9C) nonanal in the breath of rat #3 at different times.
Figure 9B:
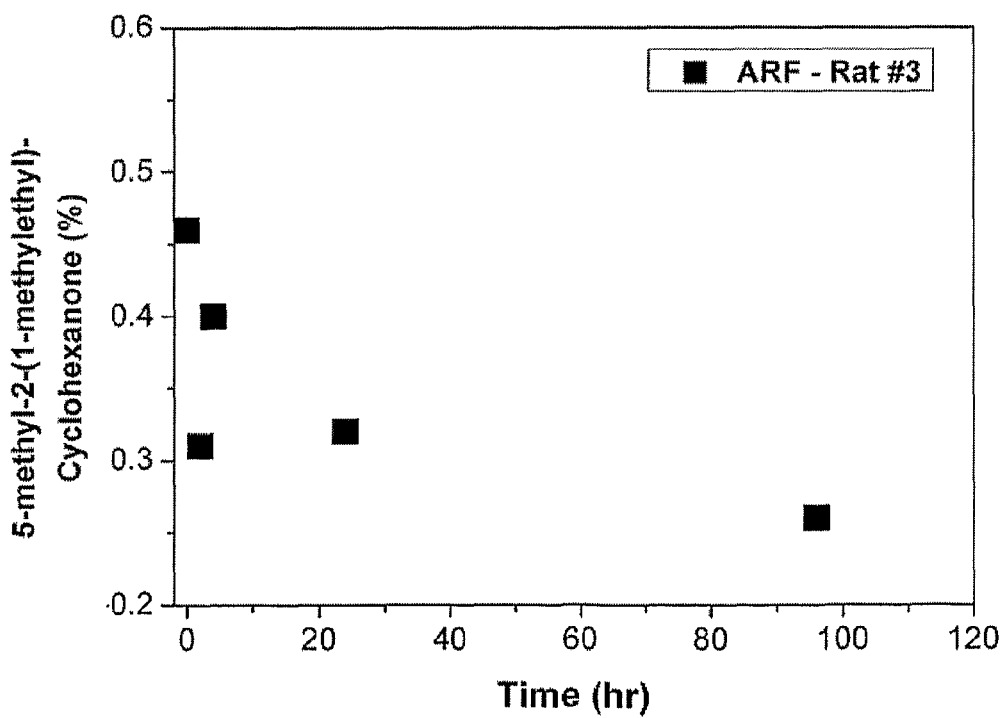
Figure 9C:
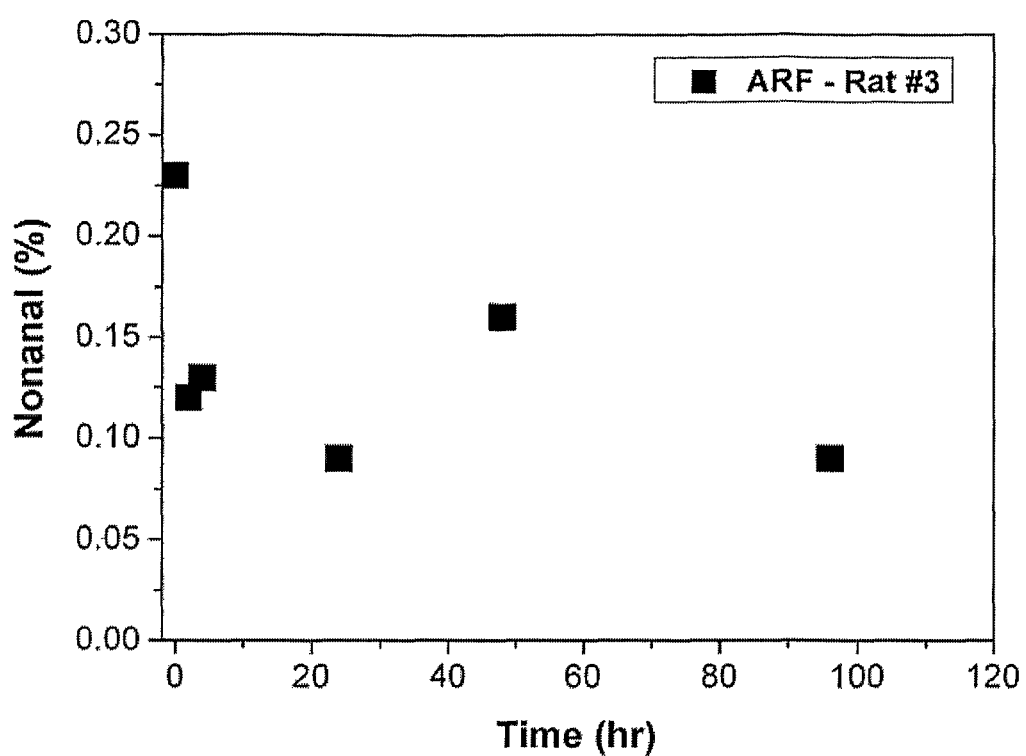

As can be seen from FIG. 8, the responses obtained from the breath of sham control by a chemiresistive random network of single-walled carbon nanotubes (SWCNTs) coated with $C_4H_9NO_5$, were almost constant over time, in consistency with its creatinine values. In contrast to the sham control, rat #3 showed a continuous decrease in the response with time. Most importantly, the decrease in response was seen at a much earlier stage in comparison to the creatinine levels. Changes in sensor response upon exposure to breath of rat #3 were observed as early as 2 hrs after the induction of acute renal failure. Hence, these results indicate that single-walled carbon nanotubes (SWCNTs) coated with $C_4H_9NO_5$ can detect acute renal failure at the very early stages of the disease, before it becomes life threatening. Without being bound by any theory or mechanism of action, the GC-MS results (FIGS. 9A-9C) indicate that sensors selectively interact (thus inducing a sensing response) with one or a combination of the following volatile organic compounds: isothiocyanato-cyclohexane, 5-methyl-2-(1-methylethyl)-cyclohexanone, and nonanal. The concentration levels of these VOCs in breath samples of sham rats remained constant throughout the experiment.

Example 9

Sensitivity of Sensors in Diagnosing Acute Renal Failure

Breath samples taken from rat #5 were analyzed using both SWCNT-based sensor and Gas-Chromatography linked to Mass-spectrometry (GC-MS) in conjugation with Solid Phase Microextraction (SPME; Divinylbenzene/Carboxen/Polydimethylsiloxane). As could be seen from Table 2, rat #5 has shown almost constant creatinine levels during the first 48 hrs after induction of acute renal failure. The creatinine levels showed an increase after 48 hrs, reaching a value of 2.2 mg %. In contrast to rats #3 and #4, rat #5 showed recovery after 48 hrs, as indicated by creatinine values of 0.7 mg % at the end of 168 hrs. The results of the sensor system of the present invention and of the GC-MS are summarized in FIGS. 10 and 11A-11C, respectively.

Figure 10:
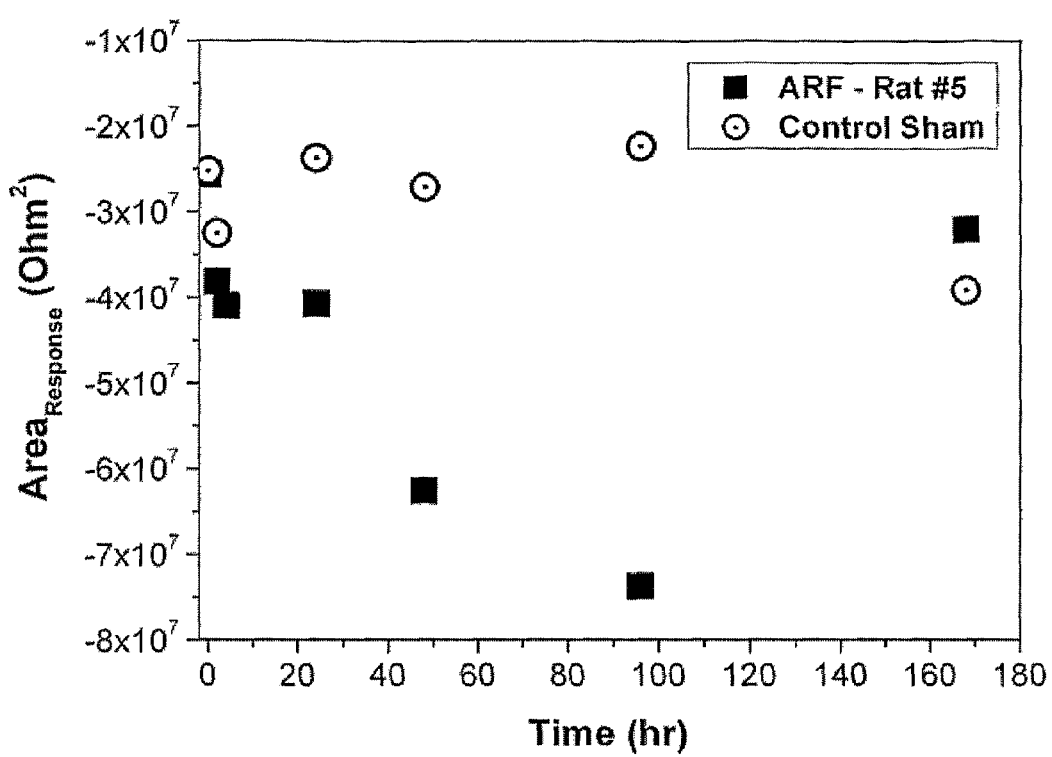
FIG. 10 shows the area under the response curve of chemiresistive random network of single-walled carbon nanotubes (SWCNTs) covered with $C_4H_9NO_5$ when exposed to a breath sample of rat #5 (full squares) and control sham (empty circles) at different times.
Figure 11A:
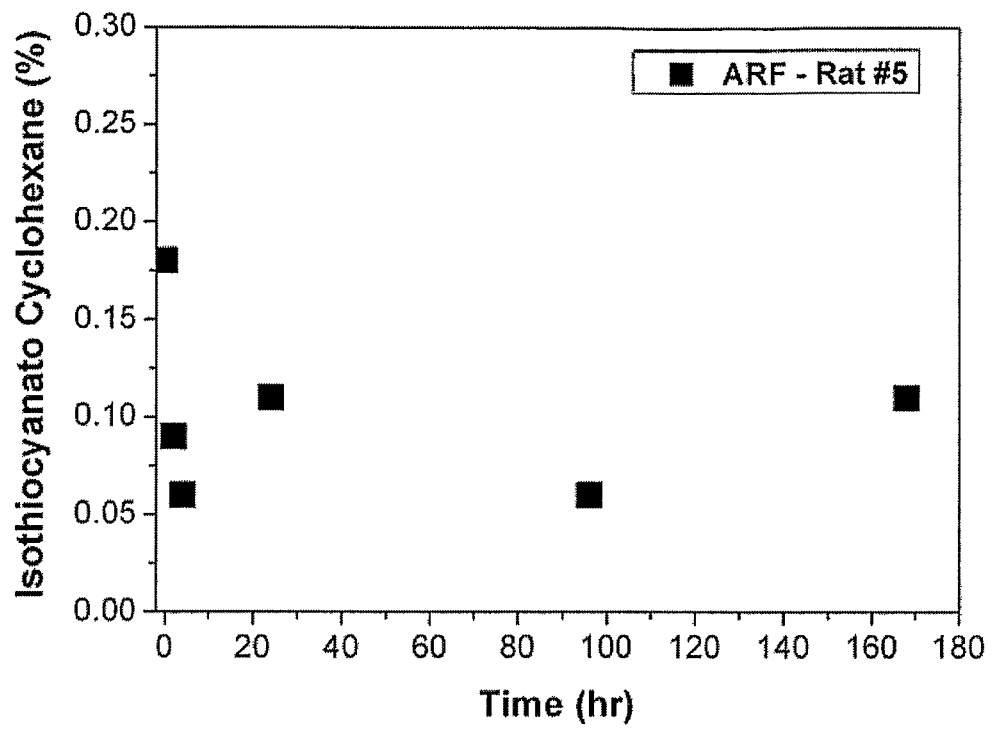
FIGS. 11A-11C show GC-MS abundance of (11A) isothiocyanato cyclohexane (11B) 5-methyl-2-(1-methylethyl)-cyclohexanone and (11C) nonanal in the breath of rat #5 at different times.
Figure 11B:
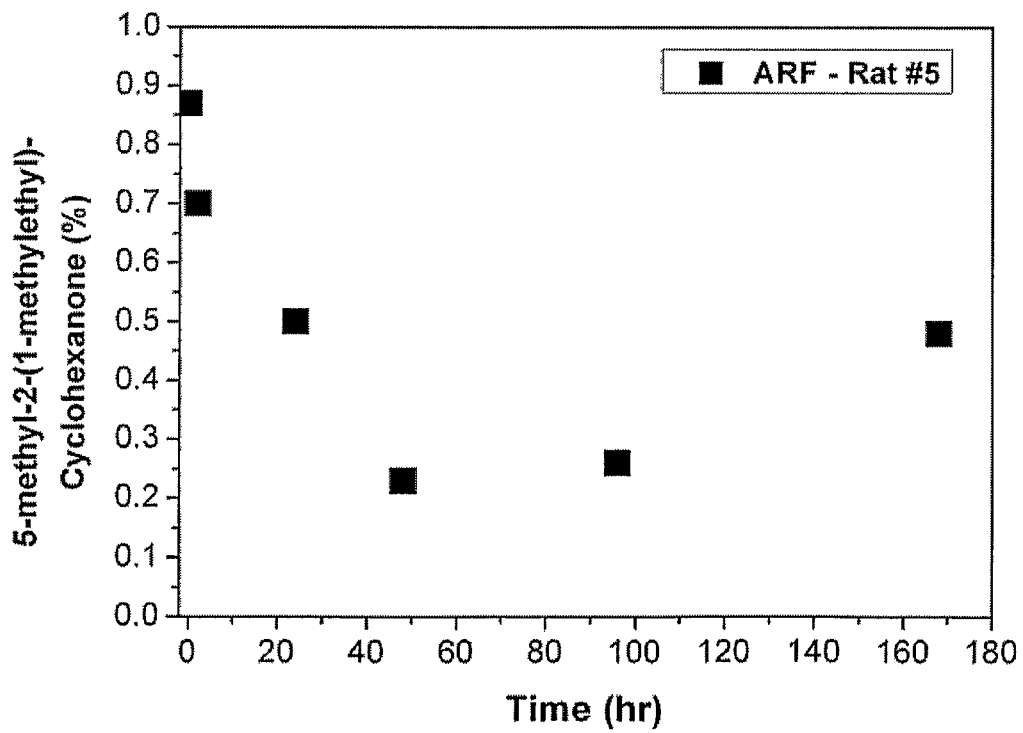
Figure 11C:
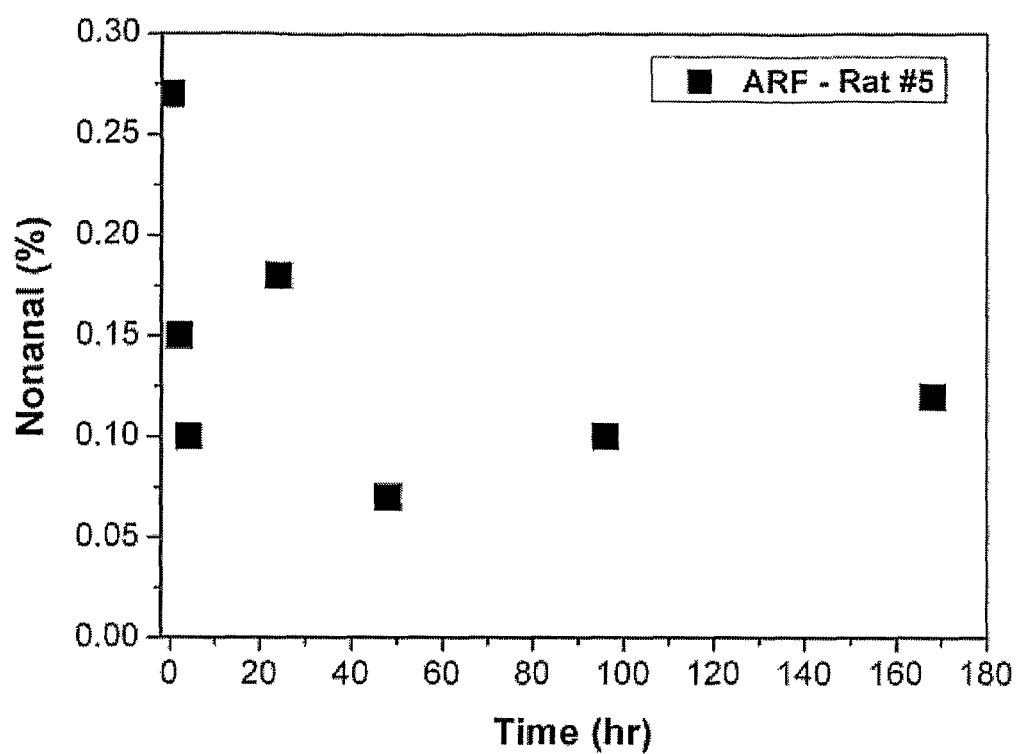

As can be seen from FIG. 10, the responses of a chemiresistive random network of single-walled carbon nanotubes (SWCNTs) coated with $C_4H_9NO_5$ to breath samples of rat #5 showed a continuous decrease in the response during the first 96 hrs, indicating deterioration in the acute renal failure condition. Of note is the negative sign of the area under the response which is indicative of a decrease in the resistivity of the chemiresistors upon exposure to the breath sample. In contrast, the responses of the sensor system to breath samples of sham rats were almost constant over time, in consistency with the creatinine values. Following 96 hrs, rat #5 showed signs of recovery wherein the response increased to a level characteristic of healthy sham (at t=0). The sensing signals were found to be in excellent consistency with the profile of creatinine levels of rat #5. GC-MS results (FIGS. 11A-11C) showed changes in the levels of isothiocyanato-cyclohexane, 5-methyl-2-(1-methylethyl)-cyclohexanone, and nonanal. The concentration levels of these VOCs in breath samples of sham rats remained constant throughout the experiment. Hence, chemiresistive $C_4H_9NO_5$-coated random network of SWCNTs provides selectivity as well as sensitivity towards one or a combination of breath VOCs indicative of renal failure.

Example 10

Sensing VOCs Indicative of Acute Renal Failure using Au Nanoparticles Capped with an Organic Coating Breath samples taken from rat #4 were analyzed using both Au nanoparticles coated with 11-mercapto-1-undecanol and GC-MS. Sensors comprising Au nanoparticles capped with an organic coating are disclosed, for example, in WO 2009/066293. As could be seen from Table 2, rat #4 has shown almost constant creatinine levels during the first 48 hrs after induction of acute renal failure. Thus, an increase in the creatinine levels was measured only after 48 hrs post induction of ARF. The results of an Au nanoparticle-based sensor system and of the GC-MS are summarized in FIGS. 12 and 13A-13D, respectively.

Figure 12:
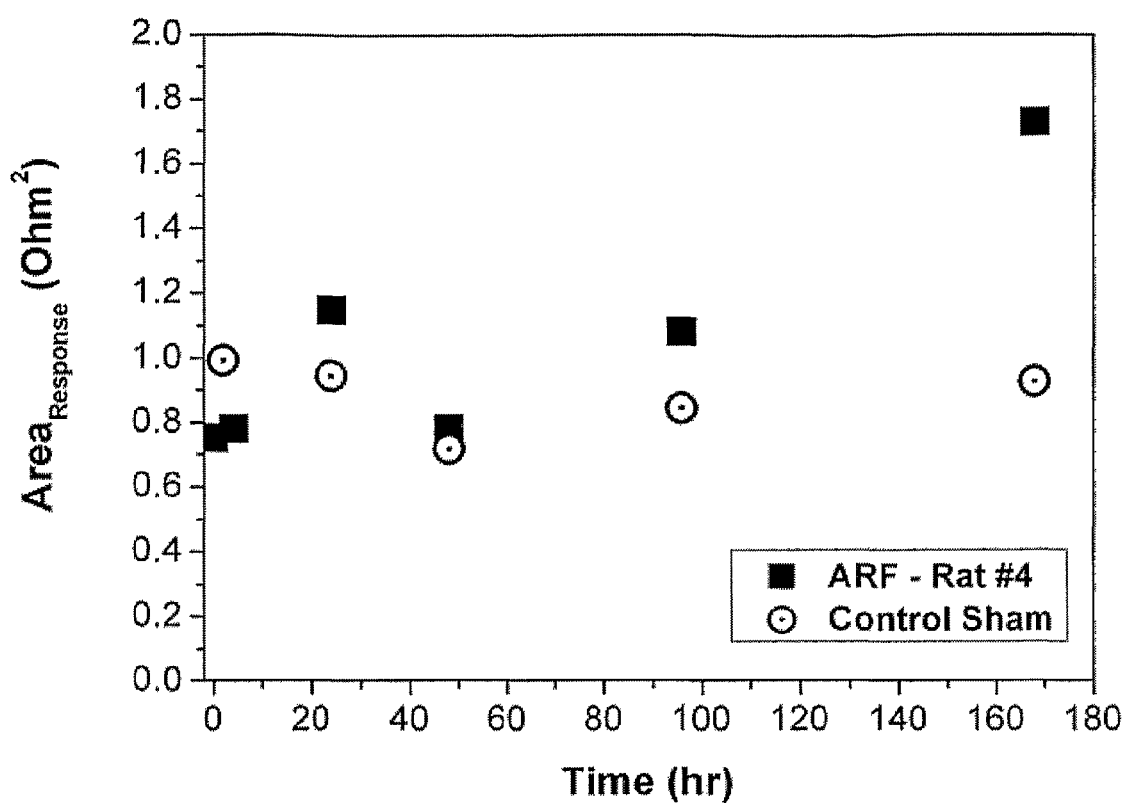
FIG. 12 shows the area under the response curve of chemiresistor based on 5 nm Au nanoparticles coated with 11-mercapto-1-undecanol when exposed to a breath sample of rat #4 (full squares) and control sham (empty circles) at different times.
Figure 13A:
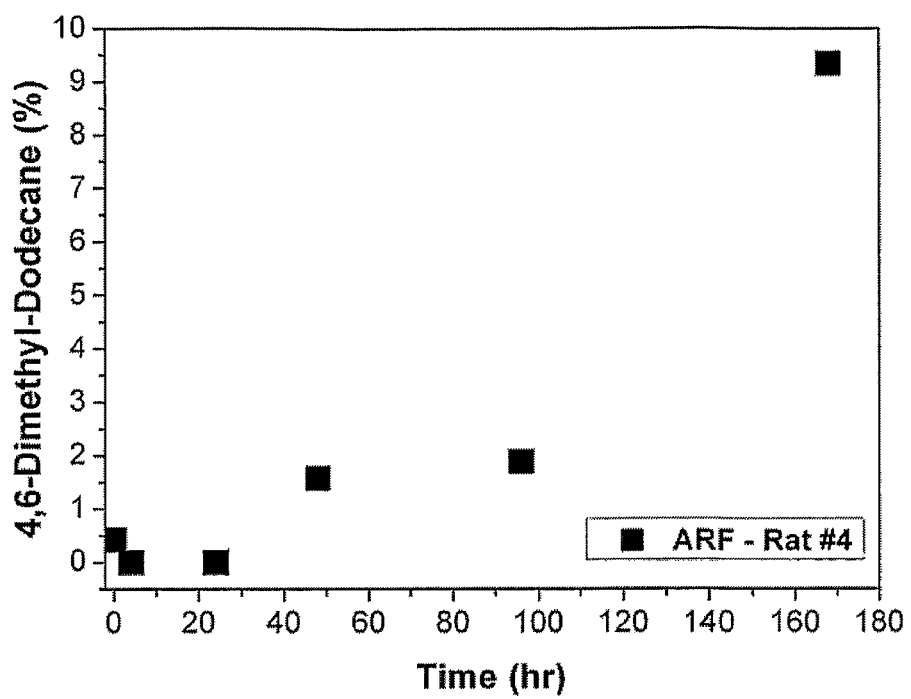
FIGS. 13A-13D show GC-MS abundance of (13A) 4,6-dimethyl-dodecane, (13B) heptadecane, (13C) hexadecane, and (13D) 4,8-dimethyl-undecane in the breath of rat #4 at different times.
Figure 13B:
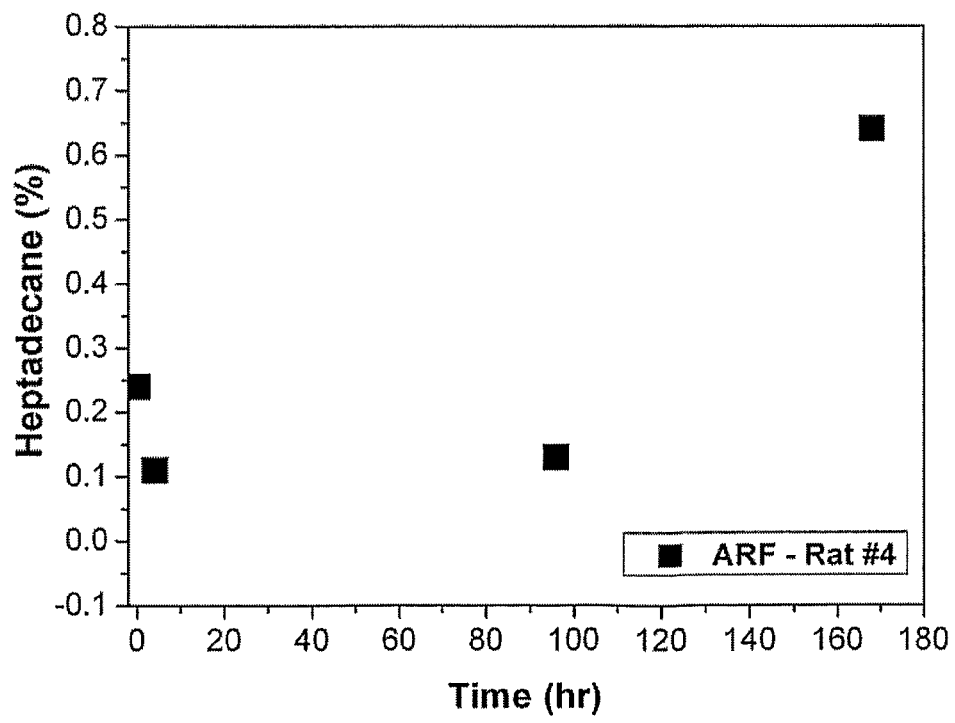
Figure 13C:
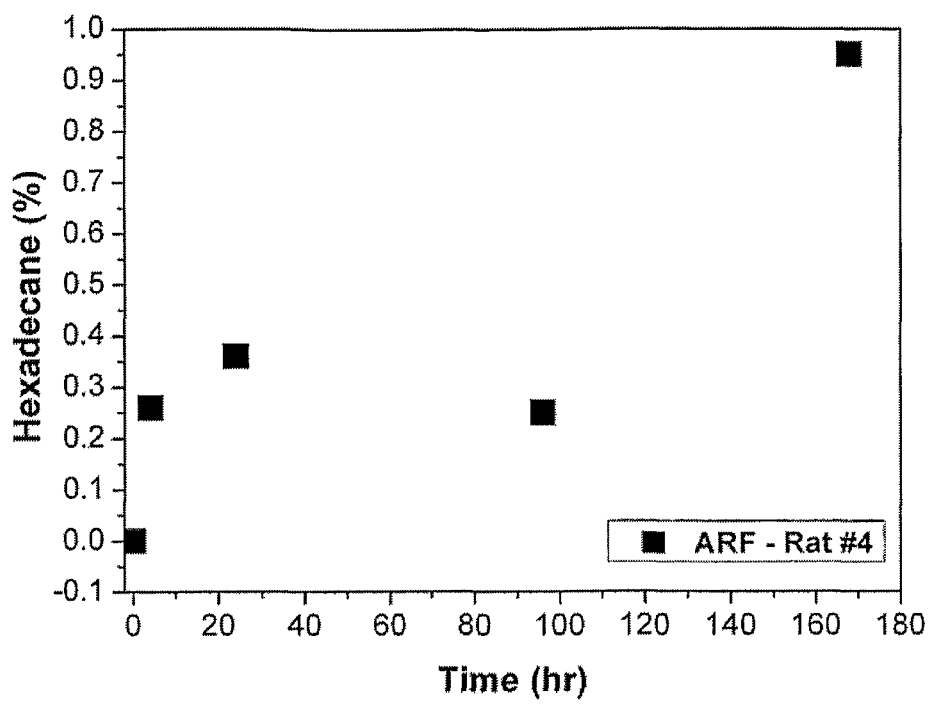
Figure 13D:
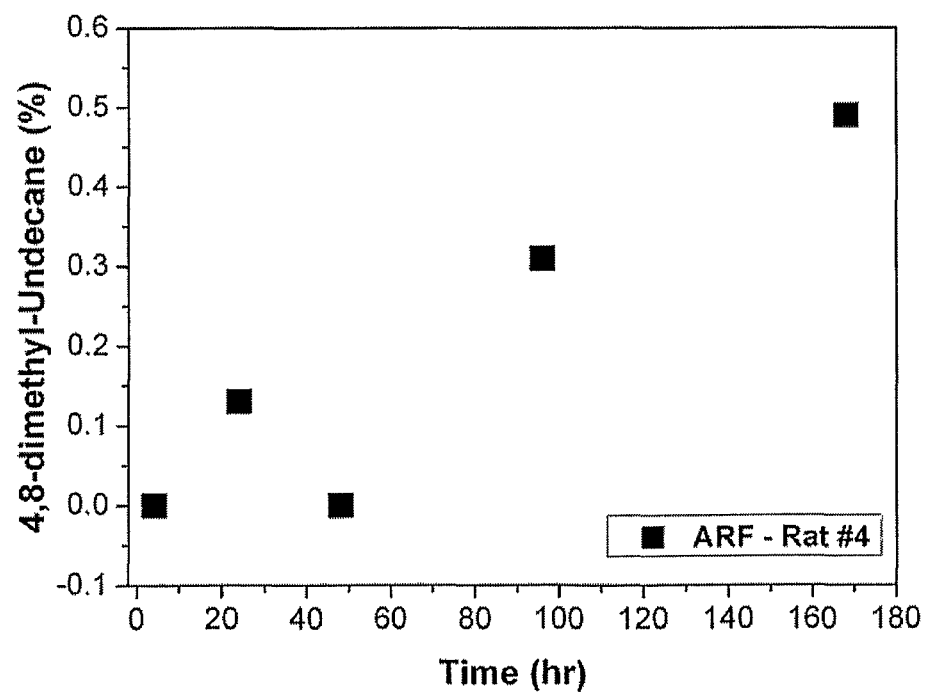

As can be seen form FIG. 12, the responses of Au nanoparticles coated with 11-mercapto-1-undecanol to breath samples of rat #4 showed a continuous increase in the response before and after the first 48 hrs post induction of ARF. Most importantly, changes in sensor responses were observed as early as 2 hrs post induction of ARF. Thus, these sensors too can detect VOCs indicative of ARF at the very early stage of the disease. GC-MS results (FIGS. 13A-13D) showed changes in the levels of 4,6-dimethyl-dodecane, heptadecane, hexadecane, and 4,8-dimethyl-undecane in the breath samples of rat #4 while no changes in the levels of these VOCs in sham rats were detected.

Example 11

Clinical Study of CRF

Exhaled breath was collected from subjects suffering from chronic renal failure and from healthy individuals. Subjects cleared the inhaled ambient air by repeatedly inhaling to total lung capacity for 5 min through a mouthpiece (purchased from Eco Medics) that contained a filter cartridge on the inspiratory port, thus removing more than 99.99% of the exogenous VOCs from the air during inspiration. Immediately after lung washout, subjects exhaled through a separate exhalation port of the mouthpiece against 10-15 cm $H_2O$ pressure to ensure closure of the vellum so that nasal entrainment of gas was excluded. Exhaled breath was comprised of a mixture of alveolar air and respiratory dead space air. Subjects then exhaled continuously into the breath collector, which in turn, automatically filled the dead space air into a separate bag and the alveolar breath into a 750 ml Mylar sampling bag (polyvinyl fluoride, purchased from Eco Medics) in a single-step process. A minimum of two bags were collected from each subject. All bags were analyzed within two days from the time of breath collection to assure accuracy of the result. In this study, 19 volunteers at the age of 28-60 participated, of which 12 were suffering from chronic renal failure immediately after diagnosis using conventional techniques, and 7 were healthy controls. The conventional techniques for diagnosis comprised measurements of the creatinine levels, BUN, ultrasound etc. The stage of the disease was determined according to MDRD, which gives an estimated GFR according to a complex formula that incorporates parameters including age, sex, PCr (plasma creatinine), race, etc. (see http://nephron.org/MDRD_GFR.cgi).

Figure 14:
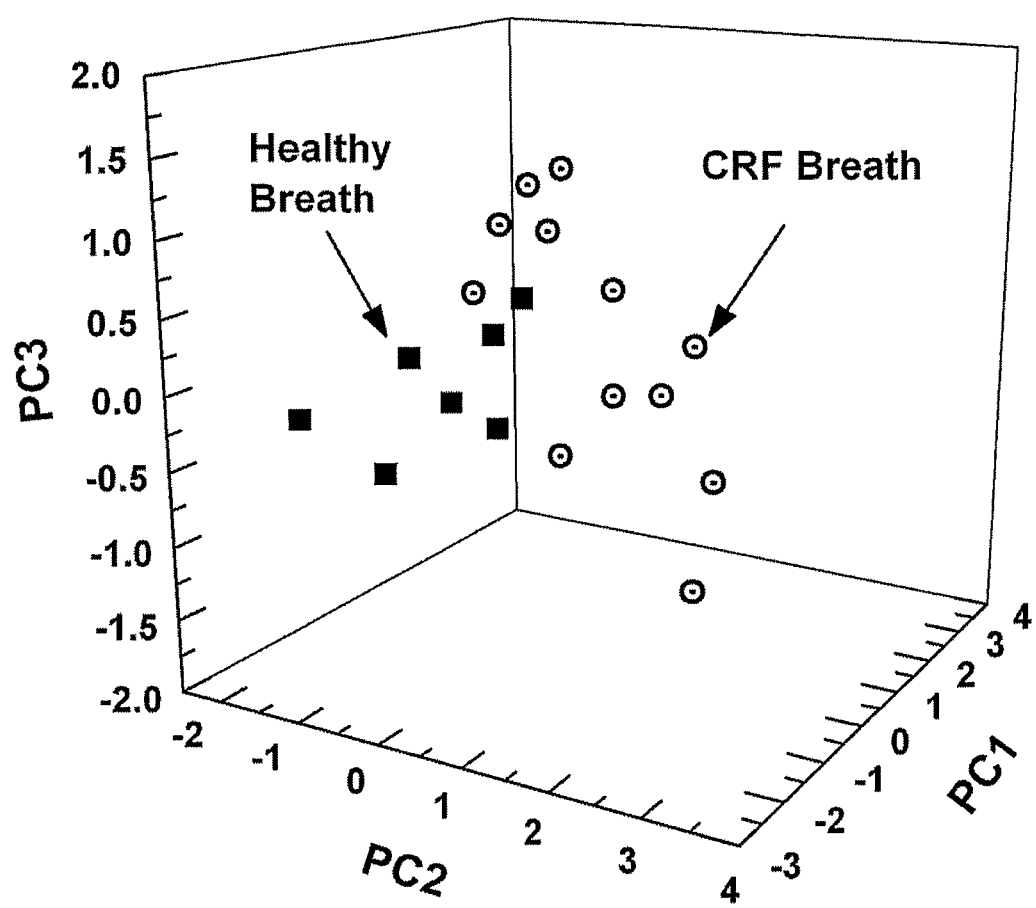
FIG. 14 shows the principal component analysis (PCA) of the data set of real breath samples. Each data point corresponds to the multidimensional $\Delta R/R_b$ of one breath sample and is the averaged response of 3-5 exposures. Healthy breath is represented by full squares and CRF breath is represented by empty circles.

The collected breath samples were exposed to an array of ten cross-reactive chemiresistive SWCNTs coated with organic films (coating) of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitro-methane ($C_4H_9NO_5$), tetracosane ($C_{24}H_{50}$)+dioctyl phthalate (($C_{24}H_{38}O_4$) (3:1 w/w), tetracosanoic acid ($C_{24}H_{48}O_2$)+dioctyl phthalate (($C_{24}H_{38}O_4$) (3:1 w/w), 1.2.5.6.9.10-hexabrormo-cyclododecane ($C_{12}H_{18}Br_6$)+dioctyl phthalate($C_{24}H_{38}O_4$) (3:1 w/w), or pentadecane ($C_{15}H_{32}$)+dioctyl phthalate ($C_{24}H_{38}O_4$) (3:1 w/w) and ten cross-reactive chemiresistive molecularly modified gold nanoparticles. The response of the 20-sensor array to both healthy and CRF breath samples was analyzed using principal component analysis (PCA). FIG. 14 shows principle components 1, 2 and 3 (PC1, PC2 and PC3) for each subject, which accounted for >90% of the variance. Clearly, no overlap between the CRF and the healthy pattern was found. Of note is the clear discrimination that was achieved without pre-concentration or dehumidification of the breath samples.

Figure 15:
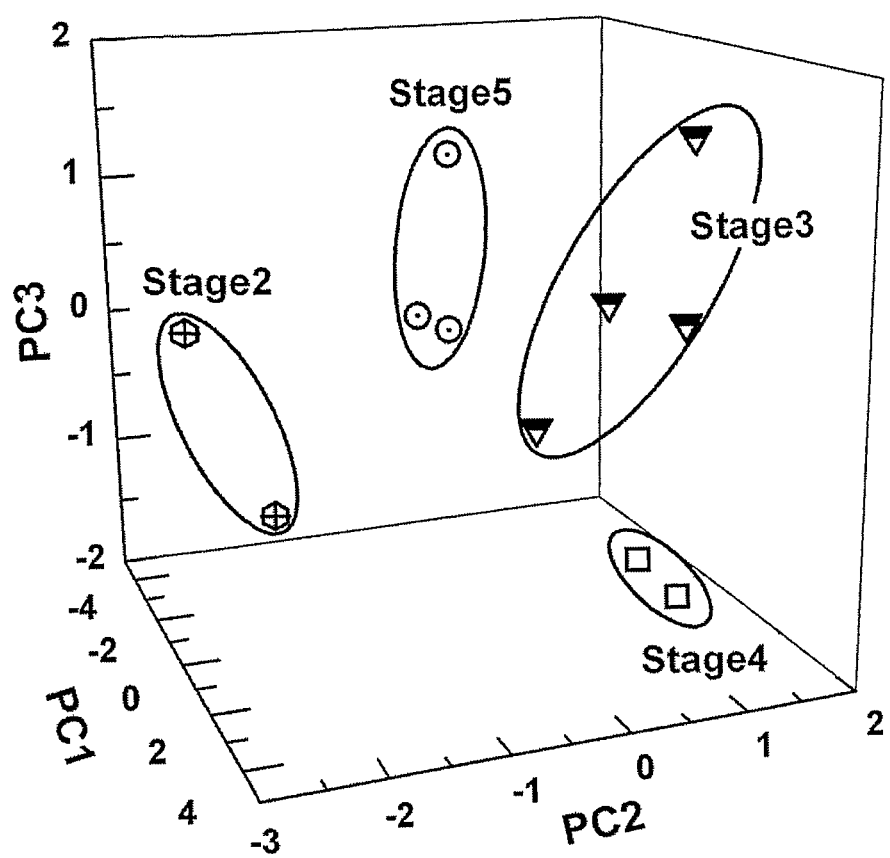
FIG. 15 shows the principal component analysis (PCA) of the data set of real breath samples. Each data point corresponds to the multidimensional $\Delta R/R_b$ of one breath sample and is the averaged response of 3-5 exposures. CRF stage II (diamonds), stage III (triangles), stage IV (squares), and stage V (circles).

The potential of using an array of chemiresistive SWCNTs coated with organic molecules combined with molecularly modified gold nanoparticles for breath analysis in order to identify and distinguish between different stages of chronic renal failure was tested. FIG. 15 shows excellent discrimination between four stages of chronic renal failure (stage II, III, IV, and V). The values of $\Delta R/R_b$ (where $R_b$ is the baseline resistance of the sensor in the absence of analyte and $\Delta R$ is the baseline-corrected steady-state resistance change upon exposure of the sensor to analyte) during the various cycles formed small, well-defined clusters in the PC plot. Hence, the array of chemiresistive SWCNT coated with organic molecules and molecularly modified gold nanoparticles shows the feasibility of not only identifying chronic renal failure, but also the feasibility of distinguishing between different stages of the disease.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The invention claimed is:

1. A method for diagnosing renal failure in a subject, the method comprising:
   (a) providing a system comprising an apparatus comprising an array of chemically sensitive sensors of single walled carbon nanotubes coated with an organic coating, wherein the organic coating comprises polymers or oligomers that are modified with at least one polar functional group; and a processing unit comprising a learning and pattern recognition analyzer wherein the learning and pattern recognition analyzer receives sensor signal output signals and compares them to stored data, (b) exposing the sensor array of the apparatus to a breath sample to detect volatile organic compounds in the breath sample, and (c) using a pattern recognition algorithm to determine the presence of the volatile organic compounds in the sample that are indicative of the renal failure in the subject, thereby providing a diagnosis of renal failure.

2. The method of claim 1, wherein the renal failure is acute renal failure, chronic renal failure, end stage renal failure, tubular interstitial disease, or glomerulonephritis; or wherein the renal failure occurs as a result of renal cancer.

3. The method of claim 1, wherein the polymers are selected from the group consisting of nafion, polyethyleneimine, methylamine dehydrogenase, poly(aniline-boronic acid), amine-terminated poly(amido amine)dendrimers, poly (4-vinylpyridine), poly(ethylene oxide), polystyrene, poly (methyl vinyl ether-co-maleic anhydride), poly(ethylene-co-vinyl acetate), poly(ethylene glycol), poly(vinyl butyral), polycarbonate, poly(4-vinyl phenol), polycaprolactone, poly-(fluorostyrene), poly(styrene-co-isoprene), poly(maleic anhydride)-co-poly(methylvinyl ether), and combinations thereof; or wherein the polymers are crosslinked polymers selected from the group consisting of cross-reactive carboxylic acid substituted poly(thiophene), cross-linked dendrimerics of 1-[4-(4-dimethylamino-phenylazo)-3-[3,5-bis[3,5-bis[3,5-bis(3-butene-1-oxy)benzyloxy]benzyloxy]benzyloxy]phenyl]-2,2,2 trifluoroethanone and 1-[4-(4-dimethylaminophenylazo)-3-[3,5-bis[3,5-bis[3,5-bis(2-propene-1-oxy)benzyloxy]benzyloxy]benzyloxy]phenyl]-2,2,2 trifluoro-ethanone, cross-linked poly(p-phenyleneethynylene) containing osmium(II) complex and aldehyde groups, and combinations thereof; or wherein the oligomers are cyclodextrins selected from the group consisting of α-cyclodextrin, β-cyclodextrin, γ-cyclodextrin, methyl-β-cyclodextrin, 2,6-dibutyl-β-cyclodextrin, hydroxypropyl-β-cyclodextrin, 2,6-di-O-methyl-β-cyclodextrin, permethylated α-cyclodextrin-$6^A$-monoalcohol nitrate, dinitrophenyl substituted β-cyclodextrin-based chiral stationary phases, β- and γ-cyclodextrins bearing 4-amino-7-nitrobenz-2-oxa-1,3-diazole functional groups, sulfated and carboxy-methylated β-cyclodextrins, mono(6-cyclohexylamino-6-deoxy)-β-cyclodextrin, mono-(6-benzyl-imino-6-deoxy)-β-cyclodextrin, mono[6-(o-amino-phenyl)imino-6-deoxy]-β-cyclodextrin, mono[6-(p-aminophenyl)imino-6-deoxy]-β-cyclodextrin, mono[6-(α-naphthyl)imino-6-deoxy]-β-cyclodextrin, hexakis (6-O-benzoyl)-α-cyclodextrin, heptakis(2,3,6-tri-O-benzoyl)-β-cyclodextrin, hexakis(6-O-benzoyl-2,3-di-O-benzyl)-α-cyclodextrin, hexakis(2,3-di-O-benzyl)-α-cyclodextrin, 2-6-amino-β-cyclodextrin, permethylated-β-cyclodextrin, 2A,3A-Alloepithio-2A,3A-dideoxy-β-cyclodextrin, and combinations thereof.

4. The method of claim 1, wherein the array of chemically sensitive sensors further comprises sensors of single walled carbon nanotubes coated with compounds selected from the group consisting of 2,5-bis(dimethylthiocarbamoyloxy) terephthalic acid diethyl ester, 2,5-bis(dimethyl-thiocarbamoyl-sulfanyl)terephthalic acid diethyl ester, 2,5-dimercaptoterephthalic acid, n-(3-trifluoroethanesulfonyloxypropyl)-anthraquinone-2-carboxamide, 3-methyl 4-(tetraethoxy) thiophene, 3-[n-succinimido(tetra-ethoxy)oxy]-4-methyl thiophene, quinacrine dihydrochloride dehydrate, lauric acid, quinacrine dihydrochloride, dihydrate phthalate, etracosanoic acid, 2,5,6,9,10-hexabromocyclododecane, and combinations thereof; or compounds selected from the group consisting of propyl gallate ($C_{10}H_{12}O_5$), anthracene ($C_{14}H_{10}$), tetracosanoic acid ($C_{24}H_{48}O_2$), tricosane ($C_{23}H_{48}$), 3-methyl-2-phenyl valeric acid ($C_{12}H_{16}O_2$), tris(hydroxymethyl)nitromethane ($C_4H_9NO_5$), tetracosane ($C_{24}H_{50}$), dioctyl phthalate(($C_{24}H_{38}O_4$)), 1,2,5,6,9,10-hexabrormo-cyclododecane ($C_{12}H_{18}Br_6$), pentadecane ($C_{15}H_{32}$), and combinations thereof; or hexa-peri-hexabenzocoronene (HBC) derivatives selected from the group consisting of $HBC-C_{6,2}$, $HBC-C_{10,6}$, $HBC-C_{14,10}$, and $HBC-C_{12}$.

5. The method of claim 1, wherein the sensors are configured in a form selected from the group consisting of capacitive sensors, resistive sensors, impedance sensors, and field effect transistor sensors.

6. The method of claim 1 further comprising the step of collecting the sample into a breath collector prior to step (b), wherein the breath collector comprises at least one of a unit for concentrating breath analytes and a dehumidifying unit.

7. The method of claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

8. The method of claim 1, wherein the array of chemically sensitive sensors further comprises sensors of metal nanoparticles capped with an organic coating.

9. The method of claim 8, wherein the metal nanoparticles are selected from the group consisting of Au, Ag, Ni, Co, Pt, Pd, Cu, and Al nanoparticles.

10. The method of claim 8, wherein the organic coating of the metal nanoparticles comprises compounds selected from the group consisting of alkylthiols, arylthiols, alkylarylthiols, alkylthiolates, ω-functionalized alkylthiolates, arenethiolates, (γ-mercaptopropyl)tri-methyloxysilane, and combinations and derivatives thereof.

11. The method of claim 1, wherein the volatile organic compounds in the sample indicative of the renal failure in the subject are selected from the group consisting of dimethylamine, trimethylamine, isopalmitate, isopropyl palmitate, isothiocyanato-cyclohexane, 5-methyl-2-(1-methylethyl)-cyclohexanone, nonanal, and 6-nitro-2-picoline.

* * * * *